United States Patent
Holets-McCormack

(10) Patent No.: US 8,329,415 B2
(45) Date of Patent: Dec. 11, 2012

(54) LYSIS REAGENT FOR USE WITH CAPTURE-IN-SOLUTION IMMUNOASSAY

(75) Inventor: Shelley R. Holets-McCormack, Waukegan, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/196,831

(22) Filed: Aug. 2, 2011

(65) Prior Publication Data

US 2011/0294140 A1 Dec. 1, 2011

Related U.S. Application Data

(60) Division of application No. 12/491,394, filed on Jun. 25, 2009, now Pat. No. 7,993,851, which is a continuation of application No. PCT/US2007/088109, filed on Dec. 19, 2007.

(60) Provisional application No. 60/878,017, filed on Dec. 29, 2006.

(51) Int. Cl.
*G01N 33/53* (2006.01)

(52) U.S. Cl. ..................... 435/7.1; 436/518

(58) Field of Classification Search .............. None
See application file for complete search history.

(56) References Cited

U.S. PATENT DOCUMENTS

| | | | |
|---|---|---|---|
| 4,624,930 A | 11/1986 | Tanswell et al. |
| 4,652,517 A | 3/1987 | Scholl et al. |
| 5,134,875 A | 8/1992 | Jensen et al. |
| 5,135,875 A | 8/1992 | Meucci et al. |
| 5,169,773 A | 12/1992 | Rosenthaler et al. |
| 5,217,971 A | 6/1993 | Takasugi et al. |
| 5,322,772 A | 6/1994 | Soldin |
| 5,350,574 A | 9/1994 | Erlanger et al. |
| 5,354,845 A | 10/1994 | Soldin |
| 5,489,668 A | 2/1996 | Morrison et al. |
| 5,498,597 A | 3/1996 | Burakoff et al. |
| 5,525,523 A | 6/1996 | Soldin |
| 5,650,228 A | 7/1997 | May |
| 5,650,288 A | 7/1997 | MacFarlane et al. |
| 5,698,448 A | 12/1997 | Soldin |
| 5,750,413 A | 5/1998 | Morrison et al. |
| 5,780,307 A | 7/1998 | Soldin |
| 5,897,990 A | 4/1999 | Baumann et al. |
| 5,955,108 A | 9/1999 | Sutton et al. |
| 5,990,150 A | 11/1999 | Matsui et al. |
| 6,054,303 A | 4/2000 | Davalian et al. |
| 6,087,134 A | 7/2000 | Saunders |
| 6,187,547 B1 | 2/2001 | Legay et al. |
| 6,197,588 B1 | 3/2001 | Gray et al. |
| 6,239,102 B1 | 5/2001 | Tiemessen |
| 6,328,970 B1 | 12/2001 | Molnar-Kimber et al. |
| 6,410,340 B1 | 6/2002 | Soldin |
| 6,541,612 B2 | 4/2003 | Molnar-Kimber et al. |
| 6,858,439 B1 | 2/2005 | Xu et al. |
| 6,913,580 B2 | 7/2005 | Stone |
| 6,998,246 B2 | 2/2006 | Schäffler et al. |
| 7,189,582 B2 | 3/2007 | Chen et al. |
| 2002/0002273 A1 | 1/2002 | Sedrani et al. |
| 2002/0022717 A1 | 2/2002 | Sedrani et al. |
| 2002/0055124 A1 | 5/2002 | Janda et al. |
| 2002/0151088 A1 | 10/2002 | Molnar-Kimber et al. |
| 2003/0157556 A1 | 8/2003 | Maggiore et al. |
| 2003/0235839 A1 | 12/2003 | McKernan et al. |
| 2004/0062793 A1 | 4/2004 | Van Dyke |
| 2004/0101429 A1 | 5/2004 | Ogawa |
| 2004/0102429 A1 | 5/2004 | Modak et al. |
| 2005/0033035 A1 | 2/2005 | Beisel et al. |
| 2005/0055126 A1 | 3/2005 | Genma et al. |
| 2005/0112778 A1 | 5/2005 | Wang et al. |
| 2005/0164323 A1 | 7/2005 | Chaudhary et al. |
| 2005/0272109 A1 | 12/2005 | Schäffler et al. |
| 2006/0003390 A1 | 1/2006 | Schäffler et al. |
| 2006/0020401 A1 | 1/2006 | Davis et al. |
| 2006/0062793 A1 | 3/2006 | Webb et al. |
| 2006/0257957 A1 | 11/2006 | Drengler et al. |
| 2008/0020401 A1 | 1/2008 | Grenier et al. |
| 2008/0160499 A1 | 7/2008 | Grenier et al. |
| 2008/0176756 A1 | 7/2008 | Siegel et al. |
| 2009/0325193 A1 | 12/2009 | Grenier et al. |
| 2009/0325197 A1 | 12/2009 | Drengler et al. |

FOREIGN PATENT DOCUMENTS

| | | |
|---|---|---|
| EP | 0293892 | 12/1988 |
| EP | 440044 A1 | 8/1991 |
| EP | 0471295 | 2/1992 |
| EP | 693132 A1 | 1/1996 |
| EP | 753744 A2 | 1/1997 |
| EP | 973805 A1 | 1/2000 |
| EP | 1244800 A1 | 10/2002 |
| EP | 2118657 A2 | 11/2009 |
| WO | WO905008 A1 | 5/1990 |

(Continued)

OTHER PUBLICATIONS

Alak et al., "Measurement of Tacrolimus (FK506) and Its Metabolites: A Review of Assay Development and Application in Therapeutic Drug Monitoring and Pharmacokinetic Studies," Therapeutic Drug Monitoring, 1997, vol. 19, 338-351.

(Continued)

*Primary Examiner* — Jacob Cheu

(74) *Attorney, Agent, or Firm* — Audrey L. Bartnicki; Jennifer Wahlsten; Weaver, Austin, Villeneuve & Sampson LLP

(57) ABSTRACT

The invention provides a lysis reagent and method for preparing a test sample for use in an assay, wherein the method yields a homogeneous lysis mixture suitable for use in automated pipetting systems without the need for a centrifugation step. The lysis reagent includes a glycol and non-specific animal immunoglobulins. Other aspects of the invention include related immunoassays and test kits.

29 Claims, 6 Drawing Sheets

FOREIGN PATENT DOCUMENTS

| | | |
|---|---|---|
| WO | WO9218527 A1 | 10/1992 |
| WO | WO9219745 A1 | 11/1992 |
| WO | WO9325533 A1 | 12/1993 |
| WO | WO9424304 A1 | 10/1994 |
| WO | WO9425022 A1 | 11/1994 |
| WO | WO9425072 A1 | 11/1994 |
| WO | WO9516691 A1 | 6/1995 |
| WO | WO9525812 A2 | 9/1995 |
| WO | WO9612018 A2 | 4/1996 |
| WO | WO9613273 A1 | 5/1996 |
| WO | WO9703654 A2 | 2/1997 |
| WO | WO9800696 A1 | 1/1998 |
| WO | WO9845333 A1 | 10/1998 |
| WO | WO9853315 A1 | 11/1998 |
| WO | WO0134816 A1 | 5/2001 |
| WO | WO2008082974 A2 | 7/2008 |
| WO | WO2008082979 A2 | 7/2008 |
| WO | WO2008082982 A1 | 7/2008 |
| WO | WO2008082984 A2 | 7/2008 |

OTHER PUBLICATIONS

Bose et al., "Characterization and Molecular Modeling of a Highly Stable Anti-Hepatitis B Surface Antigen scFv," Molecular Immunology, 2003, vol. 40, 617-631.

Clarke W., et al, "Immunoassays for therapeutic drug monitoring and clinical toxicology," Drug monitoring and clinical chemistry, 2004, 5, 95-112.

Cogill et al. (Clinical Chem 1998 vol. 44, p. 1942-1946).

Hatfield R. M. et al., "Development of an Enzyme-Linked Immunosorbent Assay for the Detection of Humoral Antibody to Pasteurella Anatipestifer," Avian Pathology, 1987, vol. 16, 123-140.

Kricka et al., "Human Anti-Animal Antibody Interferences in Immunological Assays," Clinical Chemistry, 1999, vol. 45, 942-956.

Kronquist K. E., et al., "Mechanism of alteration of the functional fraction of lipoprotein lipase in rat heart," Life Sci., 1980, 27(13), 1153-1158.

Le Meur Y, et al., "CYP3A5*3 influences sirolimus oral clearance in de novo and stable renal transplant recipients," Clin Pharmacol Ther., 2006, 80(1), 51-60.

Lee J. W., et al., "Tacrolimus (FK506): validation of a sensitive enzyme-linked immunosorbent assay kit for and application to a clinical pharmacokinetic study," Ther Drug Monit., 1997, 19(2), 201-207.

Melnikova et al., "Antigen Binding Activity of Monoclonal Antibodies After Incubation with Organic Sovents," Biochemistry (Moscow), 2000, vol. 65, No. 11, pp. 1488-1499.

Murakami et al., "On-chip micro-flow polystyrene bead-based immunoassay for quantitative detection of tacrolimus (FK506)," Analytical Biochemistry, 2004, vol. 334, pp. 11-116.

PCT International Search Report and Written Opinion for Application No. PCT/US07/10076, mailed Jul. 11, 2008, 11 pages total.

PCT International Search Report and Written Opinion for Application No. PCT/US07/88056, mailed Aug. 25, 2008, 11 pages total.

PCT International Search Report and Written Opinion for Application No. PCT/US07/88070, mailed Oct. 8, 2008, 11 pages total.

PCT International Search Report and Written Opinion for Application No. PCT/US07/88087, mailed Sep. 24, 2008, 12 pages total.

PCT International Search Report and Written Opinion for Application No. PCT/US07/88098, mailed May 27, 2008, 7 pages total.

PCT International Search Report and Written Opinion for Application No. PCT/US07/88109, mailed Sep. 24, 2008, 15 pages total.

Simamora P, et al., "Solubilization of rapamycin," Int J Pharm., 2001, 213(1-2), 25-29.

Sinha et al., "Electrostatics in Protein Binding and Function," Current Protein and Peptide Science, 2002, vol. 3, 601-614.

Sinha et al., "Understanding antibody-antigen associations by molecular dynamics simulations: Detection of important intra- and intermolecular salt bridges," Cell Biochem Biophys, 2007, vol. 47, 361-375.

Supplementary European Search Report of EP Patent Application No. 07869499.9 dated Feb. 3, 2011, 6 pages total.

Supplementary European Search Report of EP Patent Application No. EP07869487, dated Mar. 19, 2010, issued Apr. 9, 2010, 8 pages total.

Supplementary European Search Report of EP Patent Application No. EP07865858, dated Mar. 19, 2010, issued Apr. 1, 2010, 9 pages total.

Supplementary European Search Report of EP Patent Application No. EP07869508, dated Mar. 19, 2010, issued Apr. 13, 2010, 11 pages total.

Supplementary European Search Report of EP Patent Application No. EP07861291, dated Jan. 11, 2010, issued Jan. 21, 2010, 11 pages total.

Tamura et al., "A Highly Sensitive Method to Assay FK-506 Levels in Plasma ," A Transplantation Proceedings Reprint, 1987, vol. XIX (6), 23-29.

USPTO Office Action dated Aug. 21, 2009, cover sheet and pp. 1-10, Notice of reference, Information Disclosure Statement by Applicant and considered by Examiner in U.S. Appl. No. 11/490,624.

Uwatoko et al., "Characterization of Clq-Binding IgG Complexes in Systemic Lupus Erythematosus," Clinical Immunology and Immunopathology, 1984, vol. 30, 104-116.

Watson J. D. et al., "The Introduction of Foreign Genes Into Mice", Recombinant DNA, 2nd Ed., W.H. Freeman & Co., New York, 1992, 225-272.

Wilson D., et al., "Multi-center evaluation of analytical performance of the microparticle enzyme immunoassay for sirolimus," Clin Biochem., 2006, 39(4), 378-386.

PCT International Preliminary Report on Patentability for Application No. PCT/US07/88109, issued Jun. 30, 2009, 8 pages total.

Examination Report of EP Patent Application No. EP07869508, dated Mar. 7, 2012, 6 pages total.

Examination Report of EP Patent Application No. EP07869508, dated Jul. 15, 2011, 18 pages total.

Exemplary Homogeneous Single Reagent, Single Step Sample Pretreatment

Pipette 100 μL whole blood specimen into a 1.5 mL centrifuge tube

Pipette in 300 μL Lysis Reagent
(comprising, e.g., 70% Ethylene Glycol, 30% Buffer, 100 μg/mL Mouse IgG)

Vortex about 10 seconds to mix

Initiate immunoassay

LYSIS REAGENT FOR USE WITH CAPTURE-IN-SOLUTION IMMUNOASSAY

CROSS REFERENCE TO RELATED APPLICATIONS

This application is a divisional application of U.S. application Ser. No. 12/491,394, filed on Jun. 25, 2009 and issued as U.S. Pat. No. 7,993,851 on Aug. 9, 2011, which is a continuation application of PCT International Application PCT/US07/88109, filed on Dec. 19, 2007 (expired), and claims the priority of U.S. Provisional Application Ser. No. 60/878,017, filed on Dec. 29, 2006, the disclosures of each of which are hereby incorporated herein by reference in their entireties.

TECHNICAL FIELD

This invention relates to a non-denaturing lysis reagent for use with a capture-in-solution immunoassay. This lysis reagent is useful, for example, in diagnostic immunoassays of samples suspected of containing immunoglobulins to an animal species that is the same as the animal species of a capture antibody employed in the immunoassay.

BACKGROUND

Many analytes of clinical interest are taken up by cells or become complexed with one or more other components of the test sample. Accordingly, to obtain an accurate measurement of the amount of analyte present in the sample, it is preferable to treat the sample, and/or conduct the assay under conditions, such that the analyte is released from the cells or other component(s) for detection in the assay.

For example, immunosuppressant drugs such as tacrolimus, everolimus, temsorolimus and cyclosporine are effective for the treatment of organ or tissue rejection following transplant surgery, of graft versus host disease and of autoimmune diseases in humans. During immunosuppressant drug therapy, monitoring the blood concentration levels of the immunosuppressant is an important aspect of clinical care because insufficient drug levels lead to graft (organ or tissue) rejection and excessive levels lead to undesired side effects and toxicities. Blood levels of immunosuppressant are therefore measured so drug dosages can be adjusted to maintain the drug level at the appropriate concentration. Diagnostic assays for determination of immunosuppressant blood levels have thus found wide clinical use.

Initially, the immunosuppressant must be extracted and separated from the other components of the patient sample. The bulk of the immunosuppressant drug in the patient sample is present in a complex with various "carrier" molecules, such as binding proteins. Sirolimus, tacrolimus and cyclosporine are found predominately in the red blood cells of patient specimens and are associated with specific binding proteins, FKBP for sirolimus and tacrolimus, and cyclophilin for cyclosporine. To ensure an accurate measurement of the total drug concentration in the specimen, the drug bound to the binding proteins is preferably liberated prior to quantitation. This has been addressed by using detergents to lyse cells and/or organic solvents to denature the sample proteins, followed by the separation of drug from sample proteins.

Following its extraction, the drug can be measured in a number of different ways, including by immunoassay or chromatography with absorbance or mass spectrophotometric detection. Immunoassays for immunosuppressant drugs are available in a variety of formats, but all use the binding of an antibody or binding protein (e.g. FKBP) to the immunosuppressant drug. A commonly used immunoassay is an assay which involves the binding of a capture antibody to the immunosuppressant and the binding of labeled immunosuppressant (e.g. acridinium-sirolimus) to the remaining free antibody binding sites, followed by quantitation by detection of the label. A standard format for a cyclosporine immunoassay employs a mouse anti-cyclosporine monoclonal antibody bound to goat anti-mouse antibody-coated microparticles.

The above approach typically requires a separation step that removes binding proteins and other potentially interfering proteins from the sample prior to assay. For example, this approach removes antibodies that might otherwise cross-react with a component of an immunoassay carried out to determine the concentration of an immunosuppressant drug. Human samples, in particular, may contain anti-species antibodies that bind to antibodies from a particular animal species, mouse, for example, that are employed as capture or detection antibodies in the assay. Interfering anti-mouse antibodies may be present in human blood as a consequence of the previous administration of a mouse monoclonal antibody for an in vivo diagnostic procedure or as a therapeutic.

SUMMARY

The invention provides a method for preparing a test sample for use in an immunoassay employing a capture antibody. In particular embodiments, the test sample includes a human blood sample. The method entails contacting the test sample with a lysis reagent to form a lysis mixture The lysis reagent includes a glycol selected from the group consisting of ethylene glycol, propylene glycol, and an analog thereof. In exemplary embodiments, the glycol is present in the lysis reagent at a concentration in the range of about 60% to about 80%. Immunoglobulins of an animal species that is the same as the animal species of the capture antibody are included in the lysis reagent or added to the lysis mixture. In certain embodiments, the immunoglobulins include mouse immunoglobulins, such as, e.g., non-specific polyclonal mouse IgG. In exemplary embodiments, the immunoglobulins are present in the lysis reagent at a concentration in the range of about 90 µg/mL to 110 µg/mL.

In particular embodiments, the lysis reagent additionally includes at least one alcohol having five or fewer carbons.

In illustrative embodiments, the test sample is added to the lysis reagent at a ratio in the range of about 1:2 to about 1:4.

Preferably, the method does not entail centrifuging the lysis mixture. In certain embodiments, the method does not entail contacting the test sample or the lysis mixture with a detergent. In alternative embodiments, the method does entail contacting the test sample or the lysis mixture with a detergent.

Where the immunoassay detects an analyte that is bound to one or more binding proteins in the test sample, the method can additionally include contacting the test sample or the lysis mixture with an agent that releases the analyte from the binding protein(s). The releasing agent can, for example, compete with the analyte for binding to the binding protein(s). In an illustrative embodiment, the analyte includes an immunosuppressant drug, and the agent includes a different, but structurally similar, immunosuppressant drug. Wherein the analyte is a non-protein molecule, the releasing agent can include a protease that degrades said one or more binding proteins.

Another aspect of the invention is a lysis reagent mixture for use in an immunoassay employing a capture antibody. The lysis reagent mixture includes a glycol selected from the group consisting of ethylene glycol, propylene glycol, and an analog thereof. Immunoglobulins of an animal species that is the same as the animal species of the capture antibody are included in the lysis reagent mixture. In certain embodiments, the immunoglobulins include mouse immunoglobulins, such as, e.g., non-specific polyclonal mouse IgG.

In particular embodiments, the mixture additionally includes a test sample suspected of including antibodies specific for said immunoglobulins. The test sample can, for example, include a human blood sample. In variations of such embodiments, the glycol is present in the lysis reagent mixture (after addition of the test sample) at a concentration in the range of about 15% to about 20% and/or the immunoglobulins are present in the lysis reagent mixture at a concentration in the range of about 20 µg/mL to 30 µg/mL.

In certain embodiments, the lysis reagent mixture additionally includes at least one alcohol having five or fewer carbons. The lysis reagent mixture can, optionally, include a detergent.

The invention also provides an immunoassay method for determining the presence or concentration of an analyte. The method entails contacting a test sample with a lysis reagent to form a lysis mixture. The lysis reagent includes a glycol selected from the group consisting of ethylene glycol, propylene glycol, and an analog thereof. In exemplary embodiments, the glycol is present in the lysis reagent at a concentration in the range of about 60% to about 80%. Immunoglobulins of an animal species that is the same as the animal species of a capture antibody that binds analyte are included in the lysis reagent or added to the lysis mixture. In certain embodiments, the immunoglobulins include mouse immunoglobulins, such as, e.g., non-specific polyclonal mouse IgG. In exemplary embodiments, the immunoglobulins are present in the lysis reagent at a concentration in the range of about 90 µg/mL to 110 µg/mL.

The lysis mixture is contacted with a solid phase including a solid-phase affixed binding partner for the capture antibody and with the capture antibody. The capture antibody is not pre-bound to the binding partner. The contacting is carried out under conditions suitable for the capture antibody to bind to the analyte and to the solid phase-affixed binding partner, whereby the capture antibody and analyte form a solid phase-affixed immune complex.

The solid phase is contacted with a detection agent under conditions suitable for the detection agent to bind to the solid phase-affixed immune complex, followed by detection of such binding.

In exemplary embodiments, the immunoassay method includes a competitive immunoassay, the detection agent includes labeled analyte or labeled analyte analog, and signal from the label is inversely proportional to the concentration of analyte in the test sample.

In particular embodiments, the analyte includes an immunosuppressant drug, such as, for example, sirolimus, tacrolimus, everolimus, temsorolimus, zotarolimus, cyclosporine, or analogs of any of these compounds.

In particular embodiments, the lysis reagent additionally includes at least one alcohol having five or fewer carbons.

The test sample can, for example, include a human blood sample. In illustrative embodiments, the test sample is added to the lysis reagent at a ratio in the range of about 1:2 to about 1:4.

Preferably, the immunoassay method does not entail centrifuging the lysis mixture. In certain embodiments, the method does not entail contacting the test sample or the lysis mixture with a detergent. In alternative embodiments, the method does entail contacting the test sample or the lysis mixture with a detergent.

Where the immunoassay detects an analyte that is bound to one or more binding proteins in the test sample, the method can additionally include contacting the test sample or the lysis mixture with an agent that releases the analyte from the binding protein(s). The releasing agent can, for example, compete with the analyte for binding to the binding protein(s). In an illustrative embodiment, the analyte includes an immunosuppressant drug, and the agent includes a different, but structurally similar, immunosuppressant drug. Wherein the analyte is a non-protein molecule, the releasing agent can include a protease that degrades said one or more binding proteins.

Another aspect of the invention is a test kit including: (a) a capture antibody; (b) a lysis reagent including a glycol selected from the group consisting of ethylene glycol, propylene glycol, and an analog thereof; and (c) immunoglobulins of an animal species that is the same as the animal species of the capture antibody. Optionally the test kit further comprises (d) labeled analyte (e.g., employed as a tracer reagent for detection). In certain embodiments, the lysis reagent and immunoglobulins are combined and packaged in a single container. The test kit can additionally contain a solid phase including a solid-phase affixed binding partner for the capture antibody, wherein the solid phase and the capture antibody are packaged in separate containers. In particular embodiments, the test kit contains a control composition including the at least one analyte of (a).

In certain embodiments, the immunoglobulins are mouse immunoglobulins, such as non-specific polyclonal mouse IgG.

In particular embodiments, the analyte includes an immunosuppressant drug, such as, for example, sirolimus, tacrolimus, everolimus, temsorolimus, zotarolimus, cyclosporine, or analogs of any of these compounds.

In exemplary embodiments, the glycol is present in the lysis reagent at a concentration in the range of about 60% to about 80%. The immunoglobulins can be present in the lysis reagent, for example, at a concentration in the range of about 90 µg/mL to 110 µg/mL.

In particular embodiments, the lysis reagent additionally includes at least one alcohol having five or fewer carbons. The test kit can, optionally, include a detergent. Where the immunoassay detects an analyte that is bound to one or more binding proteins in the test sample, the test kit can additionally include an agent that releases the analyte from the binding protein(s). The releasing agent can, for example, compete with the analyte for binding to the binding protein(s). In an illustrative embodiment, the analyte includes an immunosuppressant drug, and the agent includes a different, but structurally similar, immunosuppressant drug. Wherein the analyte is a non-protein molecule, the releasing agent can include a protease that degrades said one or more binding proteins.

An exemplary test kit includes: (a) a capture antibody capable of binding specifically to at least one immunosuppressant drug selected from the group consisting of sirolimus, tacrolimus, everolimus, temsorolimus, zotarolimus and cyclosporine; (b) a lysis reagent including: (i) a glycol selected from the group consisting of ethylene glycol, propylene glycol, and an analog thereof; and (ii) immunoglobulins of an animal species that is the same as the animal species of a capture antibody that binds the analyte; (c) a solid phase including a solid-phase affixed binding partner for the capture antibody, wherein the solid phase and the capture antibody are provided in separate containers; and (d) a control composition including the at least one immunosuppressant drug of (a). In other embodiments the test kit optionally further comprises (e) labeled analyte (e.g., employed as a tracer reagent for detection).

BRIEF DESCRIPTION OF THE DRAWINGS

FIG. 3 shows a flowchart illustrating sample preparation for a cyclosporine assay using a homogeneous, single-reagent, single-step method. In this approach, endogenous interferents, such as HAMA, are present in the lysis mixture.

DETAILED DESCRIPTION

Figure 1:
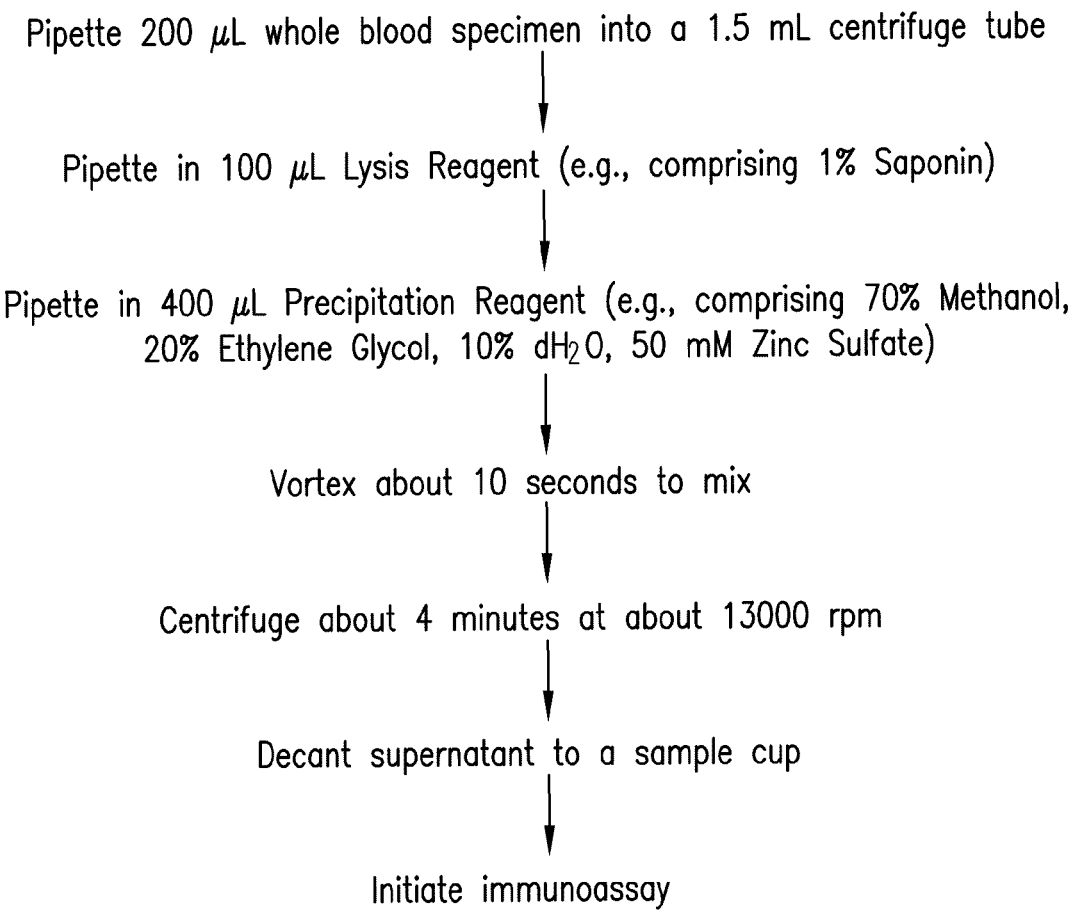
FIG. 1 shows a flowchart illustrating sample preparation for a cyclosporine assay using a two-reagent, two-step method (heterogeneous lysis mixture). This method is characterized by lysis and release of cyclosporine from its binding protein, followed by centrifugation to remove sample proteins. In this approach, the assay is unaffected by endogenous interferents, such as human anti-mouse antibodies (HAMA) because these are removed prior to assay.
Figure 2:
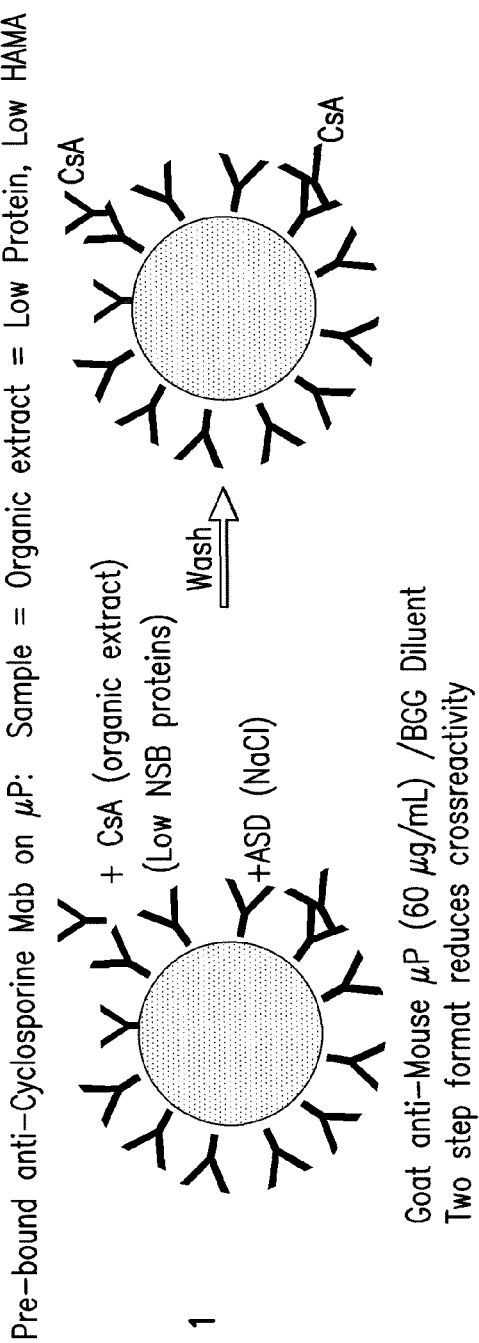
FIG. 2 is a diagrammatic illustration of competitive immunoassay conducted in conjunction with the two-reagent, two-step method. The assay uses a magnetic microparticle (μP) as a solid phase. A goat anti-mouse antibody (GAM) is attached to the microparticle as a binding partner for an anti-cyclosporine monoclonal antibody (Mab; capture antibody). The Mab is pre-bound to the GAM. The sample mixture (produced by the process of FIG. 1) containing the cyclosporine analyte (CsA) is contacted with the microparticles and with a suitable assay-specific diluent (ASD) containing NaCl. The pre-bound anti-cyclosporine Mab binds CsA in the sample. After a wash step, the microparticles are contacted with a tracer, consisting of acridinylated CsA (labeled analyte), which binds to sites on the anti-cyclosporine Mab that are unoccupied by sample CsA. The signal measured is inversely proportional to the concentration of analyte in the sample.
Figure 2:
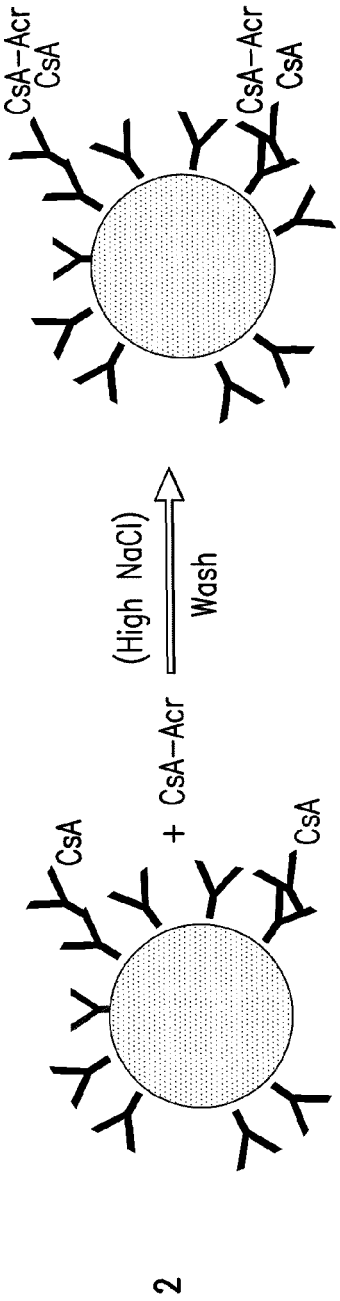
Figure 4:
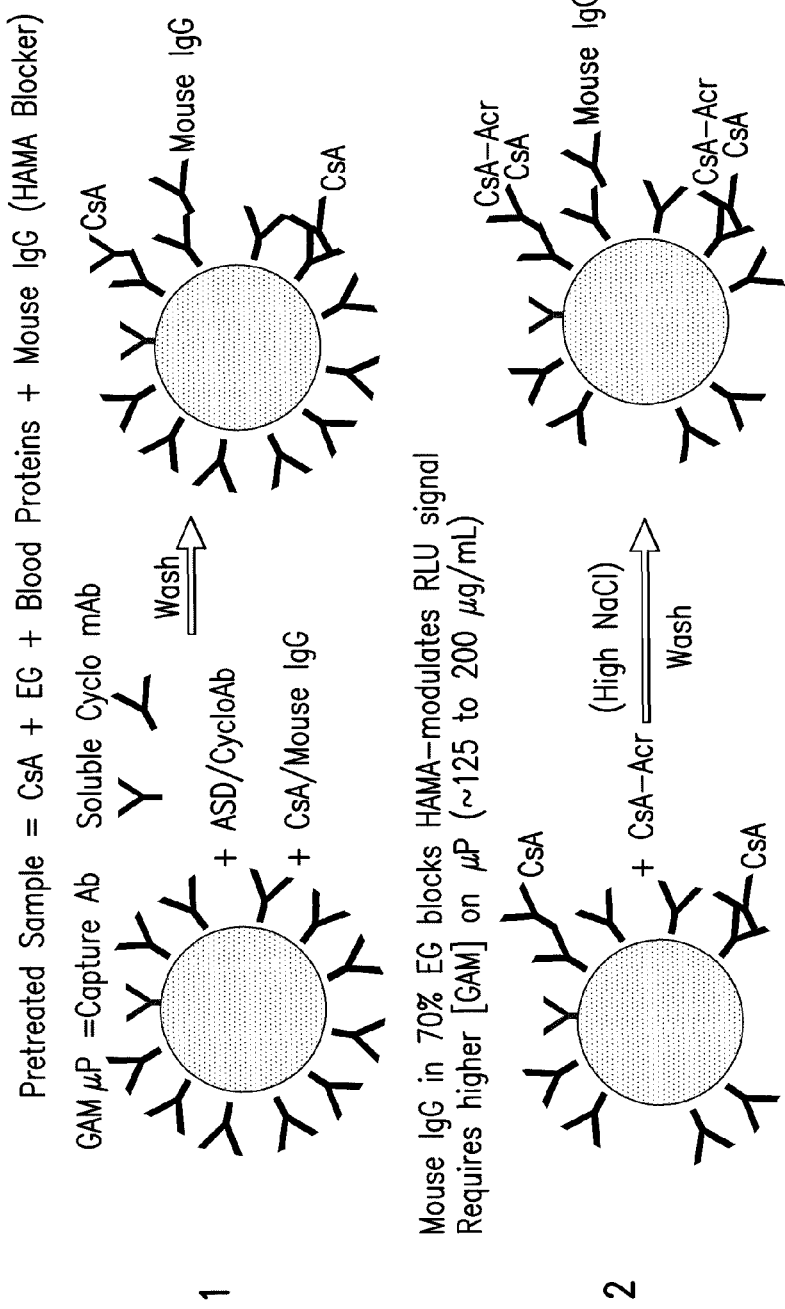
FIG. 4 is a diagrammatic illustration of competitive immunoassay conducted using a capture-in-solution immunoassay. The assay uses a magnetic microparticle (μP) as a solid phase, with an attached goat anti-mouse antibody (GAM). The GAM acts as a binding partner for an anti-cyclosporine monoclonal antibody (Mab; capture antibody), but the Mab is not pre-bound to the GAM, rather the Mab (e.g., at 200 ng/mL) is provided to the assay mixture via the assay-specific diluent (ASD). The lysis mixture (produced by the process of FIG. 3) contains the cyclosporine analyte (CsA) and mouse IgG (HAMA blocker). This lysis mixture is contacted with the anti-cyclosporine Mab-containing assay-specific diluent (ASD) and with the microparticles. The anti-cyclosporine Mab binds CsA in the sample and becomes bound the microparticles via the GAM antibody. After a wash step, the microparticles are contacted with a tracer, consisting of acridinylated CsA (labeled analyte), which binds to sites on the anti-cyclosporine Mab that are unoccupied by sample CsA. The signal measured is inversely proportional to the concentration of analyte in the sample. Such an assay can be carried out, for example, on an automated ARCHITECT® i2000® analyzer (Abbott Laboratories, Abbott Park, Ill.).

The invention relates to a non-denaturing lysis reagent that can be mixed with a test sample to produce a homogeneous lysis mixture that can be assayed without a subsequent separation step. The methods and reagents of the invention, in effect, neutralize the potential interference of sample antibodies specific for immunoglobulins of an animal species that is the same as the animal species of an antibody, e.g., a capture antibody employed in a subsequent immunoassay.

The lysis reagent can be used, for example, in the homogeneous pretreatment of whole blood in a capture-in-solution immunoassay for cyclosporine. Non-specific mouse IgG can be included in the lysis reagent to reduce or prevent interference from human anti-mouse antibody (HAMA) that may be present in patient specimens. The lysis reagent is mixed with a blood sample to create a homogeneous mixture of blood constituents that can be readily pipetted manually or by an automated pipetting system.

Definitions

Terms used in the claims and specification are defined as set forth below unless otherwise specified.

An "immunosuppressant drug" or "immunosuppressant", as used herein, refers to a therapeutic compound, either small molecule or antibody based, that has the same or similar chemical structure to either rapamycin (sirolimus) or cyclosporine, also known as cyclosporine A. Any known or hereafter developed analog of either rapamycin or cyclosporine is considered an immunosuppressant herein. Preferred immunosuppressants include sirolimus, tacrolimus, everolimus, temsorolimus, zotarolimus and cyclosporine. Tacrolimus and cyclosporine are calcineurin inhibitors that suppress early activation of the immune system's T lymphocytes through inhibition of cytokines such as interleukin 2 In contrast, the primary target of sirolimus, everolimus and zotarolimus is mammalian target of rapamycin (mTOR), a specific cell-cycle regulatory protein. The inhibition of mTOR leads to suppression of cytokine-driven T-lymphocyte proliferation.

The chemical formula of cyclosporine is in Formula A. The chemical formula of sirolimus (rapamycin) is in Formula B. The chemical formula of the structural difference of everolimus (RAD) from sirolimus is in Formula C.

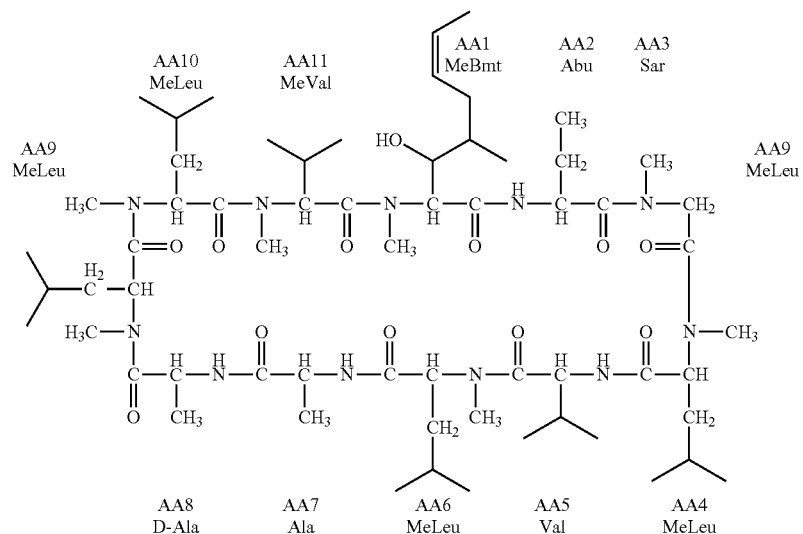

A

B cyclosporine

C

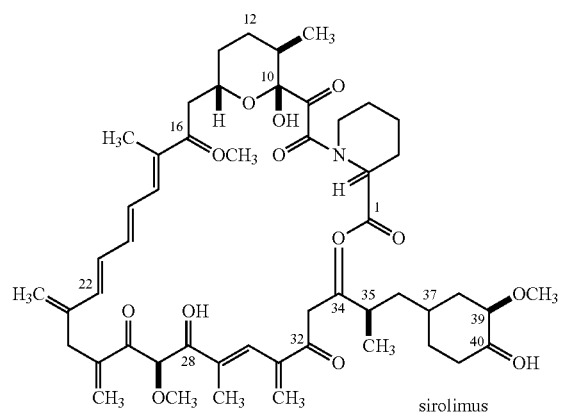

sirolimus

Numerous derivatives or analogs of cyclosporine have been prepared. The invention comprises lysis reagents, lysis methods, assays and assay kits for cyclosporine or any of its analogs.

Numerous derivatives or analogs of rapamycin have been prepared. For example, these include the preparation of ester mono- and di-ester derivatives of rapamycin (PCT International Application WO 92/05179), 27-oximes of rapamycin (European Patent EP 0 467606); 42-oxo analog of rapamycin (U.S. Pat. No. 5,023,262); bicyclic rapamycins (U.S. Pat. No. 5,120,725); rapamycin dimers (U.S. Pat. No. 5,120,727); silyl ethers of rapamycin (U.S. Pat. No. 5,120,842); and arylsulfonates and sulfamates (U.S. Pat. No. 5,177,203). Rapamycin was recently synthesized in its naturally occurring enantiomeric form (K. C. Nicolaou et al., *J. Am. Chem. Soc.,* 1993, 115, 4419-4420; S. L. Schreiber, *J. Am. Chem. Soc.,* 1993, 115, 7906-7907; S. J. Danishefsky, *J. Am. Chem. Soc.,* 1993, 115, 9345-9346. The invention comprises lysis reagents, lysis methods, assays and assay kits for rapamycin or any of its analogs.

Another immunosuppressant analog of rapamycin is FK-506, also known as tacrolimus, which was isolated from a strain of *S. tsukubaensis*. FK-506's chemical formula is published in European Patent EP 0 293 892 B1. Analogs of FK-506 include the related natural products FR-900520 and FR-900523, which differ from FK-506 in their alkyl substituent at C-21, and were isolated from *S. hygroscopicus yakushimnaensis*. Another analog, FR-900525, produced by *S. tsukubaensis*, differs from FK-506 in the replacement of a pipecolic acid moiety with a proline group. The invention comprises lysis reagents, lysis methods, assays and assay kits for FK-506 or any of its analogs. Temsorolimus is another ester derivative of sirolimus which can be monitored with the invention.

ABT-578 [40-epi-(1-tetrazolyl)-rapamycin], known better today as zotarolimus, is a semi-synthetic macrolide triene antibiotic derived from rapamycin. Zotarolimus' structure is shown in Formula D.

Formula D.
The isomers of zotarolimus

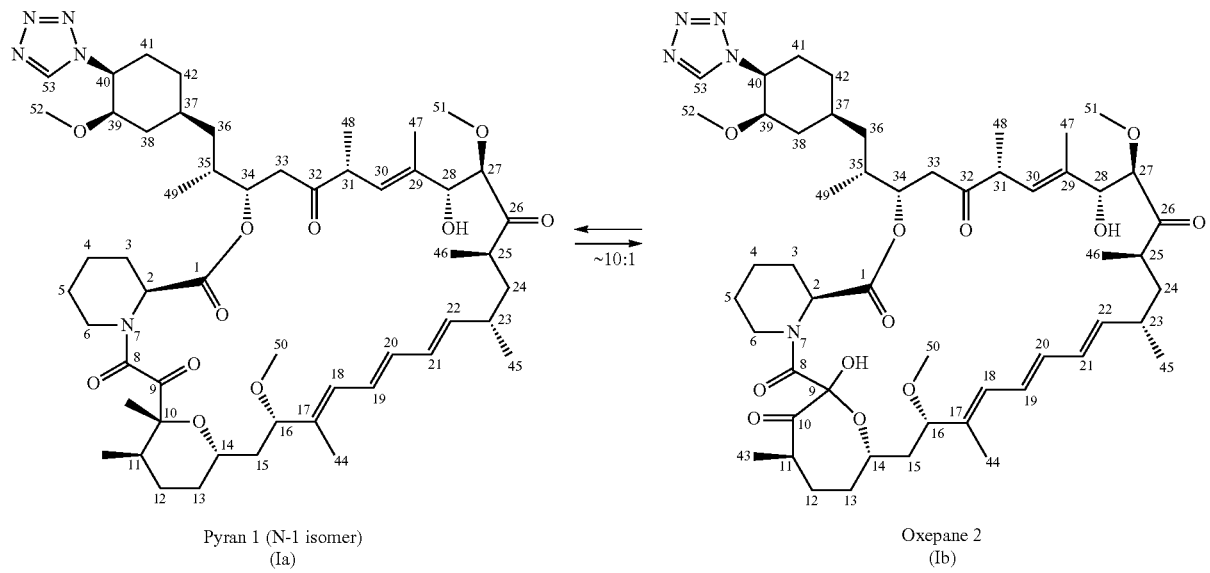

Pyran 1 (N-1 isomer)
(Ia)

Oxepane 2
(Ib)

~10:1

As used herein with reference to an immunosuppressant drugs, the term "structurally similar" indicates that the drugs have sufficiently similar structures that the drugs bind competitively to at least one common binding partner (e.g., a binding protein).

The term "test sample" refers to a component, tissue or fluid of an animal's body that is the source of the immunosuppressant drug analyte. These components, tissues and fluids include human and animal body fluids such as whole blood, serum, plasma, synovial fluid, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens. Preferably, the test sample is a human peripheral blood sample.

As used herein, an "antibody" refers to a protein consisting of one or more polypeptides substantially encoded by immunoglobulin genes or fragments of immunoglobulin genes. This term encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab')2, a dimer of Fab which itself is a light chain joined to VH-CH$_1$ by a disulfide bond. The F(ab')2 may be reduced under mild conditions to break the disulfide linkage in the hinge region thereby converting the (Fab')$_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology.

Thus, the term "antibody," as used herein, also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv), in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker (Huston, et al. (1988) Proc. Nat. Acad. Sci. USA, 85: 5879-5883). While the VH and VL are connected to each as a single polypeptide chain, the VH and VL domains associate non-covalently. The scFv antibodies and a number of other structures convert the naturally aggregated, but chemically separated, light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

"Analyte," as used herein, refers to the substance to be detected, which may be suspected of being present in the test sample. The analyte can be any substance for which there exists a naturally occurring specific binding partner or for which a specific binding partner can be prepared. Thus, an analyte is a substance that can bind to one or more specific binding partners in an assay.

A "binding partner," as used herein, is a member of a binding pair, i.e., a pair of molecules wherein one of the molecules binds to the second molecule. Binding partners that bind specifically are termed "specific binding partners." In addition to the antigen and antibody binding partners commonly used in immunoassays, other specific binding partners can include biotin and avidin, carbohydrates and lectins, complementary nucleotide sequences, effector and receptor molecules, cofactors and enzymes, enzyme inhibitors and enzymes, and the like. Immunoreactive specific binding partners include antigens, antigen fragments, antibodies and antibody fragments, both monoclonal and polyclonal, and complexes thereof, including those formed by recombinant DNA methods.

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site (s)).

An antibody that specifically binds an immunosuppressant drug is said to be "specific for" that immunosuppressant drug.

The term "capture agent" is used herein to refer to a binding partner that binds to analyte, preferably specifically. Capture agents can be, or can become, attached to a solid phase. As used herein, the binding of a solid phase-affixed capture agent to analyte forms a "solid phase-affixed" complex.

A capture agent that is an antibody is termed a "capture antibody."

The term "labeled detection agent" is used herein to refer to a binding partner that binds to analyte, preferably specifically, and is labeled with a detectable label or becomes labeled with a detectable label during use in an assay.

A "detectable label" includes a moiety that is detectable or that can be rendered detectable.

As used with reference to a labeled detection agent, a "direct label" is a detectable label that is attached, by any means, to the detection agent.

As used with reference to a labeled detection agent, an "indirect label" is a detectable label that specifically binds the detection agent. Thus, an indirect label includes a moiety that is the specific binding partner of a moiety of the detection agent. Biotin and avidin are examples of such moieties that are employed, for example, by contacting a biotinylated antibody with labeled avidin to produce an indirectly labeled antibody.

As used herein, the term "indicator reagent" refers to any agent that is contacted with a label to produce a detectable signal. Thus, for example, in conventional enzyme labeling, an antibody labeled with an enzyme can be contacted with a substrate (the indicator reagent) to produce a detectable signal, such as a colored reaction product.

As used herein, the term analyte analog refers to any compound that shares has the ability to bind to a binding partner for a particular analyte, preferably specifically. Thus, an analyte analog can bind to an antibody that specifically binds to analyte. If analyte an analyte analog are combined with the binding partner (e.g., antibody); the analyte and analyte analog compete for binding to the binding partner.

As used herein, a "glycol analog" is any glycol having from two to six carbon atoms.

A lysis reagent is, as described further herein, a reagent that is employed to lyse cells. A "lysis reagent mixture" or "lysis mixture" is the mixture that is formed by adding lysis reagent to test sample, or vice versa. The lysis mixture optionally includes additional components.

A lysis mixture is said to be "homogeneous" when it is sufficiently free of large particulates to allow accurate and reliable pipetting (either manually or using an automated system).

I. Sample Collection and Processing

The methods of the invention are generally carried out on test samples derived from an animal, preferably a mammal, and more preferably a human.

The methods of the invention can be carried out using any sample that may contain the analyte of interest (e.g., an immunosuppressant drug), such as a blood sample.

The sample is collected by any standard technique and then contacted with a lysis reagent (which also may be referred as a "pretreatment reagent"). Generally, the lysis reagent lyses any cells and optimally assists with solubilization of any analyte that is present in a test sample (e.g., by assisting the release of the analyte from any endogenous analyte binding present the sample). Preferably the lysis reagent employed herein is a homogeneous mixture that does not require a precipitation or separation step prior to addition of capture antibody or initiation of the immunoassay. The lysis reagent as described herein includes a glycol having from two to six carbon atoms. Glycols suitable for use in the lysis reagent include, for example, ethylene glycol, propylene glycol, and analogs thereof, as well as mixtures of such glycols. In particular embodiments, the glycol is present in the lysis reagent at a concentration in the range of about 60% to about 80%, for example, about 65%, about 70%, or about 75%. In exemplary, preferred embodiments, the glycol concentration in the lysis reagent is 70%. As those skilled in the art readily appreciate, these percentages can vary depending on the amount of lysis reagent added to the sample to form the lysis mixture. Thus, higher or lower concentrations can also be employed.

To prepare the sample for use in an immunoassay, immunoglobulins of an animal species that is the same as the animal species of an assay antibody are included in the lysis reagent or added to the lysis mixture. In particular embodiments, the assay employs a capture antibody, and immunoglobulins of an animal species that is the same as the animal species of the capture antibody are included in the lysis reagent or added to the lysis mixture. In exemplary embodiments, the antibody (e.g., capture antibody) is a mouse antibody, and the immunoglobulins are mouse immunoglobulins, such as, for example, non-specific polyclonal mouse IgG. The immunoglobulins are present in the lysis reagent at a concentration in the range of about 90 µg/mL to 110 µg/mL, for example, about 90 µg/mL, about 100 µg/mL, or about 105 µg/mL. In exemplary, preferred embodiments, the immunoglobulin concentration is 100 µg/mL. As those skilled in the art readily appreciate, these concentrations can vary depending on the amount of lysis reagent added to the sample to form the lysis mixture. Thus, higher or lower concentrations can also be employed.

The immunoglobulins are conveniently provided to the lysis mixture in the form of a solution, for example, in the lysis reagent itself. In this case, the solution can include a buffer, which can assist in preventing the immunoglobulins from substantially precipitating. Suitable buffers include physiological buffers that do not interfere with the immunoassay to be performed. Tris or Triethanolamine (TEA) buffer can, for example, be employed. The pH of the buffer (and resulting lysis reagent including the buffer solution) can range from about 2.0 to about 10.0, optionally from about 4.0 to about 9.0, preferably from about 7.0 to about 8.5, even more preferably from about 7.5 to about 8.0, or, about 7.0, about 7.5, about 8.0, or about 8.5. Thus, an exemplary lysis reagent can include about 70% ethylene glycol, 30% Tris or TEA, and 100 µg/mL polyclonal mouse IgG. This lysis reagent can be produced, for example, by mixing 7 mL ethylene glycol with 3 mL of 100 or 333 mM Tris or TEA pH 7.5 or 8.0, followed by addition of 100 µg/mL polyclonal mouse IgG.

In particular embodiments, at least one alcohol having five or fewer carbons is included in the lysis reagent or added to the lysis mixture. In preferred variations of such embodiments, the lysis reagent includes the alcohol(s). Alcohols suitable for use in the invention include, for example, methanol, ethanol, propanol, and mixtures thereof. In particular embodiments, the ratio of glycol to alcohol is in the range of 5:1 to about 1:5, 4:1 to about 1:4, 2:1 to about 1:2, or about 1:1 (volume:volume). In more particular embodiments, the ratio of glycol to alcohol is in the range of about 4:1 to about 1:2.

The lysis mixture can formed by any mixing technique at any desirable temperature to contact any chosen amount of the sample with the lysis reagent. The sample is contacted with a sufficient volume of lysis reagent to lyse the cells in the sample and produce a homogeneous mixture. For an exemplary lysis reagent including about 70% ethylene glycol, 30% Tris or TEA, and 100 µg/mL polyclonal mouse IgG, as described above, sample can be added to the lysis reagent at a ratio in the range of about 1:3 (volume:volume). Other sample:lysis reagent volume ratios that can be employed include about 2:1, about 1:1, about 1:2, about 1:3, about 1:4, about 1:5, or about 1:10 (volume:volume), or any range including these values as endpoints, depending on the lysis reagent composition.

For example, about 100 µL to about 600 µL of blood sample can be mixed with about 50 µL to about 1200 µL of the lysis reagent for up to about five minutes. In certain embodiments, the lysis mixture is formed by mixing 100 µL of blood sample with 300 µL of lysis reagent and vortexing vigorously for 5-10 seconds. In preferred embodiments, lysis is complete in less than a minute at room temperature.

In particular embodiments, the glycol concentration of the lysis reagent mixture (i.e., after addition of sample) is in the range of about 15% to about 20%, and the concentration of added immunoglobulins is in the range of about 20 µg/mL to 30 µg/mL The lysis reagent of the invention can be employed without any added detergent. However, in certain embodiments, one or more detergents can be added, if desired. Detergents typically do not foam in the presence of the lysis reagent, and thus lysis mixtures prepared according to the invention are amenable to automated pipetting, regardless of whether a detergent is included. If included in a lysis mixture intended for immunoassay, the detergent is preferably present at a concentration that does not interfere with the immunochemistry. Suitable detergents include CHAPS, deoxycholate, and non-ionic detergents, such as saponin. Detergent can be employed at concentrations in the range of about 0.01% to 0.1%, more preferably about 0.1%.

In particular embodiments, where the analyte is bound to one or more binding proteins in the test sample, the method can additionally entail contacting the test sample with an agent that releases the analyte from the binding protein(s). This agent can be included in the lysis reagent, if desired. The agent can, for example, be one that competes with the analyte for binding to the binding protein(s). The agent is generally selected so that it will not affect the results of the assay to be carried out. Thus, for instance, if the assay is an immunoassay, the agent is typically one that the relevant antibody does not cross-react with. Where the analyte is an immunosuppressant drug, the agent can be a different, but structurally similar, immunosuppressant drug. For example, sirolimus and tacrolimus both bind FKBP, and, for this reason, sirolimus can be used to release tacrolimus from FKBP and vice versa. Any subsequent immunoassay will generally employ an antibody that distinguishes between sirolimus and tacrolimus.

Where the analyte is a non-protein molecule, a protease can be employed to release the analyte from binding protein(s). The protease used in the method should be one that can degrade the binding protein, thereby releasing the analyte for assay and can be inactivated without adversely affecting the sensitivity and the precision of the assay to be carried out. Care should be taken in obtaining enzymes free from other contaminating enzymes that might not be inactivated by the method of inactivation used. Otherwise, any residual proteolytic activity could degrade an antibody used in a subsequent immunoassay. Exemplary proteases include proteinase K, subtilisin, dispase, thermolysin, trypsin, ficin, bromelain, and combinations thereof.

Proteinase K (Sigma Chemical Co., St. Louis, Mo.) is a nonspecific, Ca-dependent protease that can be inactivated by heat (65° C. or higher) and by specific protease inhibitors, such as phenyl methyl sulfonyl fluoride (PMSF, Boehringer Mannheim, Indianapolis, Ind.) or diisopropylfluorophosphate (DFP, Calbiochem, La Jolla, Calif.). Subtilisin (Sigma) is also a nonspecific, Ca-dependent protease that can be inactivated by heat (55° C. or higher), although it can be inhibited by acidic pH or a specific protease inhibitor, such as PMSF, DFP or aprotinin.

Dispase (Boehringer Mannheim or Sigma or Calbiochem) and thermolysin (Sigma or Boehringer Mannheim) are Ca-dependent metalloproteases, which can be inactivated by EDTA, at a concentration of about 5 mM, for example. When dispase and thermolysin combined are used as the protease, proteolysis is preferably inactivated by addition of a divalent cation chelator, such as EDTA, at a concentration of about 5 mM, for example, in the presence of a zinc salt, e.g., $ZnSO_4$, at a concentration of about 40 mM, for example.

Trypsin (Worthington Biochemical Corp., Freehold, N.J.) cleaves proteins specifically at the carboxyl side of lysine or arginine residues and can be inhibited by heat (90° C. or higher) or specifically inhibited by many agents, including aprotinin (Aprotinin injection formerly marketed as Trasylol®, by Bayer, West Haven, Conn.; inhibitor still available from Calbiochem, La Jolla, Calif., and other vendors), leupeptin (Sigma-Aldrich, St. Louis, Mo. or Boehringer Mannheim), PMSF, or specific trypsin inhibitors derived from soybean, lima bean or egg white (Worthington or Sigma-Aldrich). Ficin is a thiol protease that can be inactivated by $HgCl_2$, at a concentration of about 2 mM, for example. Bromelain is also a thiol protease and can be inactivated by bromelain inhibitor (Sigma-Aldrich).

In particular embodiments, the concentration of protease is high enough to degrade the binding proteins within about 30 minutes, preferably within about 20 minutes, yet low enough to allow efficient inactivation of the enzyme. Accordingly, the concentration of protease is preferably be in the range of about 0.5 to 2.0 units/mL, more preferably about 1 unit/mL.

After lysis and release from binding proteins, if applicable, the analyte can be measured using a capture-in-solution immunoassay, without the need to centrifuge the sample.

II. Immunoassays

A. In General

Immunoassays according to the invention can be used for the qualitative identification and/or the quantification of analyte in a test sample. These methods are applicable, for example, to immunoassays of immunosuppressant drugs, such as rapamycin (sirolimus), tacrolimus, everolimus, temsorolimus, zotarolimus, cyclosporine, and analogs of any of these compounds. Such immunoassays can be carried out by combining a lysis reagent with the test sample to form a lysis mixture, as described above. The lysis mixture can be contacted with at least one antibody specific for the analyte under conditions suitable for binding of the antibody to the analyte, if present, to form an assay mixture, and binding of the antibody to the analyte is then detected.

In preferred embodiments, a capture-in-solution immunoassay is employed. This format makes use of a capture antibody that binds the analyte to be detected, preferably specifically. In this format, the lysis mixture is contacted with a capture antibody and with a solid phase that includes a solid phase-affixed binding partner for the capture antibody. The capture antibody is not pre-bound to the binding partner. The contacting of these three components (lysis mixture, capture antibody, and solid phase with affixed binding partner) produces an assay mixture and can be carried out substantially, simultaneously or in any sequence, under conditions suitable for the capture antibody to bind to any analyte present in the sample and to the solid phase-affixed binding partner, whereby the capture antibody and analyte form a solid phase-affixed immune complex. In preferred embodiments, the capture antibody is provided as a separate assay component from the assay component including the solid phase, with its affixed binding partner. For example, the capture antibody can be provided in an assay diluent. In particular embodiments, the concentration of the capture antibody in the assay diluent is generally such that the exogenous immunoglobulin (e.g., polyclonal mouse IgG) is present in the assay mixture in molar excess over the capture antibody. The added immunoglobulin will compete somewhat with the capture antibody for binding to the solid phase-affixed binding partner. To offset this effect, the concentration of solid phase-affixed binding partner can be increased, for example, by about 2-, about 3-, about 4-, or about 5-fold.

In particular embodiments, the formation of the solid phase-affixed immune complex including the capture antibody and analyte is followed by a wash step to remove or reduce the concentration of non-specifically bound constituents of the assay mixture.

For analyte detection, the solid phase is contacted with a detection agent under conditions suitable for the detection agent to bind, preferably specifically, to the solid phase-affixed immune complex. As those of skill in the art appreciate, the capture antibody can bind specifically to the analyte, or the detection agent can bind specifically to the immune complex (e.g., via bound analyte or via unoccupied positions on the capture antibody), or both. In certain embodiments, an additional wash step is carried out, e.g., under high salt conditions, to reduce background signal. Binding of the detection agent is measured to provide an indication of the presence or concentration of analyte in the test sample.

In certain embodiments, enhanced assay sensitivity can be achieved by contacting the lysis mixture with the antibody in the presence of a salt concentration of greater than about 0.4 M (e.g., from about 0.5 M to about 5.0 M). In particular embodiments, the salt concentration is less than or equal to about 4.0 M (e.g., from about 0.5 M to about 4.0 M). In exemplary embodiments, the salt concentration is about 2.0 M (e.g., from about 1.5 M to about 2.5 M, particularly about 1.8 M, about 1.9 M, about 2.0 M, about 2.1 M, or about 2.2M). Suitable salts can include, for example, any of the following anions: fluoride, chloride, bromide, iodide, thiocyanate, acetate, citrate, and bisulfate. In particular embodiments, the salt includes a monovalent anion, such as, for example: fluoride, chloride, bromide, iodide, thiocyanate, and acetate. In preferred embodiments, the salt includes chloride, e.g., a chloride salt of an alkali metal (e.g., lithium, sodium, potassium, rubidium, cesium). Generally, the salt employed is soluble under the assay conditions. Sodium chloride is highly soluble under most conditions, and can thus be conveniently used to enhance assay sensitivity in a wide variety of immunoassays according to the invention.

The salt can be provided to the assay mixture in any convenient manner and can be present before, or added after, contact between the lysis mixture and the antibody. In particular embodiments, the salt is provided in an assay diluent, which can also optionally include one or more other components, in addition to water (such as, for example, a buffer). The salt concentration in the assay diluent will vary, depending on the desired final salt concentration and on the amount of diluent added to the assay mixture. For example, an assay diluent having a salt concentration of about 4.0 M could be added to an equal volume of assay mixture to provide a final salt concentration of about 2.0 M.

B. Antibodies

In immunoassays for the qualitative or quantitative detection of an analyte in a test sample, at least one antibody that binds to the analyte is contacted with a lysis mixture suspected of containing the analyte to form an antibody-analyte immune complex. To detect immunosuppressant drugs, any suitable antibodies that bind to the particular drug can be used in immunoassay according to the invention. Antibodies to each of rapamycin (sirolimus), tacrolimus, zotarolimus, cyclosporine and everolimus are known in the art and/or are commercially available, and any of these can be used. It is preferred to use the monoclonal antibody that is a component of Abbott Laboratories' commercially available IMx® Sirolimus assay (Abbott Laboratories, Abbott Park, Ill.) for measuring sirolimus., or any other Sirolimus assay kit marketed by Abbott Laboratories (e.g., for use on a different commercial automated platform).

An exemplary protocol for producing an antibody specific for an immunosuppressant drug is as follows. Female RBf/Dnj mice are administered 3 monthly boosts of a drug-27-CMO-tetanus toxoid immunogen followed by an immunization with drug-42-HS-tetanus toxoid preparation on the 4th month. Seven months later, an intrasplenic pre-fusion boost is administered to the animal using the drug-27-CMO-tetanus toxoid immunogen 3 days prior to the fusion. Splenic B-cells are then isolated and used in a standard polyethylene (PEG) fusion with the SP2/0 myeloma. Confluent cultures are screened for anti-drug activity 10-14 days later in a microtiter EIA and positive cultures are then cloned using limiting dilution cloning technique. The resulting clones are isolated and scaled up in IMDM w/FBS (Invitrogen Corp., Carlsbad, Calif.) tissue culture medium and the secreted antibody is affinity purified using Protein A. An exemplary, preferred antibody generated using sirolimus as the drug can be used in immunoassays for sirolimus, everolimus and zotarolimus.

An exemplary, preferred antibody for use in immunoassays for tacrolimus is described in M. Kobayashi et al., "A Highly Sensitive Method to Assay FK-506 Levels in Plasma", at pp 23-29 of "FK-506 A Potential Breakthrough in Immunosuppression", *A Transplantation Proceedings Reprint*, Supplement 6, Vol. XIX, October, 1987, Editors T. Starzl, L. Makowka and S. Todo, published by Grune & Stratton, Inc., Philadelphia, Pa.

An exemplary, preferred antibody for use in immunoassays for cyclosporine is the monoclonal antibody that is a component of Abbott Laboratories' commercially available TDx and AxSym® cyclosporine assays for measuring cyclosporine.

C. Detection

The antibody-analyte immune complexes can then detected using any suitable technique. For example, an antibody can be labeled with a detectable label to detect the presence of the antibody-analyte complex. The selection of a particular label is not critical, but the chosen label must be capable of producing a detectable signal either by itself or in conjunction with one or more additional substances.

Useful detectable labels, their attachment to antibodies and detection techniques therefore are known in the art. Any detectable label known in the art can be used. For example, the detectable label can be a radioactive label, such as, $^3$H, $^{125}$I, $^{35}$S, $^{14}$C, $^{32}$P, $^{33}$P; an enzymatic label, such as horseradish peroxidase, alkaline peroxidase, glucose 6-phosphate dehydrogenase, etc.; a chemiluminescent label, such as, acridinium derivatives, luminol, isoluminol, thioesters, sulfonamides, phenanthridinium esters, etc.; a fluorescent label, such as, fluorescein (5-fluorescein, 6-carboxyfluorescein, 3'6-carboxyfluorescein, 5(6)-carboxyfluorescein, 6-hexachlorofluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemi* (1996), which is a combined handbook and catalogue published by Molecular Probes, Inc., Eugene, Oreg., each of which is incorporated herein by reference. Preferred labels for use with the invention are chemiluminescent labels such as acridinium-9-carboxamide. Additional detail can be found in Mattingly, P. G., and Adamczyk, M. (2002) Chemiluminescent N-sulfonylacridinium-9-carboxamides and their application in clinical assays, in *Luminescence Biotechnology: Instruments and Applications* (Dyke, K. V., Ed.) pp 77-105, CRC Press, Boca Raton.

The detectable label can be bound to analyte, analyte analog, or antibody either directly or through a coupling agent. An example of a coupling agent that can be used is EDAC (1-ethyl-3-(3-dimethylaminopropyl) carbodiimide, hydrochloride), which is commercially available from Sigma-Aldrich (St. Louis, Mo.). Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

Alternatively, a second antibody that binds to analyte and that contains a detectable label can be added to the lysis mixture and used to detect the presence of the antibody-analyte complex. Any suitable detectable label can be used in this embodiment.

D. Exemplary Formats

The immunoassays of the invention can be conducted using any format known in the art, such as, but not limited to, a sandwich format, a competitive inhibition format (including both forward or reverse competitive inhibition assays) or a fluorescence polarization format. In preferred embodiments, the format is one suited to the capture-in-solution approach described above. The exemplary formats described below are described in terms of assaying an immunosuppressant drug. However, as those of skill in the art appreciate, the described formats are applicable to any analyte.

In immunoassays for the quantitative detection of an immunosuppressant, such as a preferred sandwich type format, at least two antibodies are employed to separate and quantify the drug in the lysis mixture. More specifically, the at least two antibodies bind to different parts of the drug, forming an immune complex which is referred to as a "sandwich". Generally, one or more antibodies can be used to capture the immunosuppressant in the test sample (these antibodies are frequently referred to as a "capture" antibody or "capture" antibodies) and one or more antibodies are used to bind a detectable (namely, quantifiable) label to the sandwich (these antibodies are frequently referred to as the "detection" antibody or "detection" antibodies). In a sandwich assay, it is preferred that both antibodies binding to the drug are not diminished by the binding of any other antibody in the assay to its respective binding site. In other words, antibodies should be selected so that the one or more first antibodies brought into contact with a lysis mixture suspected of containing an immunosuppressant do not bind to all or part of the binding site recognized by the second or subsequent antibodies, thereby interfering with the ability of the one or more second or subsequent antibodies to bind to the drug. In a sandwich assay, the antibodies, and preferably, the at least one capture antibody, are used in molar excess amounts relative to the maximum amount of drug expected in the lysis mixture. For example, from about 5 µg/mL to about 1 mg/mL of antibody per mL of solid phase containing solution can be used.

In one embodiment, the at least one first capture antibody can be bound to a solid support which facilitates the separation of the first antibody-drug complex from the test sample. The solid support or "solid phase" used in the inventive immunoassay is not critical and can be selected by one skilled in the art. A solid phase or solid support, as used herein, refers to any material that is insoluble, or can be made insoluble by a subsequent reaction. Useful solid phases or solid supports are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (a registered trademark of Abbott Laboratories, Abbott Park, Ill.), which are red blood cells "fixed" by pyruvic aldehyde and formaldehyde, and others. Suitable methods for immobilizing peptides on solid phases include ionic, hydrophobic, covalent interactions and the like. The solid phase can be chosen for its intrinsic ability to attract and immobilize the capture agent. Alternatively, the solid phase can comprise an additional receptor that has the ability to attract and immobilize the capture agent. The additional receptor can include a charged substance that is oppositely charged with respect to the capture agent itself or to a charged substance conjugated to the capture agent. As yet another alternative, the receptor can be any specific binding partner which is immobilized upon (attached to) the solid phase and which has the ability to immobilize the capture agent through a specific binding reaction. The receptor molecule enables the indirect binding of the capture agent to a solid phase material before the performance of the assay or during the performance of the assay.

Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind the drug. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

It is within the scope of the present invention that the solid phase also can comprise any suitable porous material with sufficient porosity to allow access by detection antibodies and a suitable surface affinity to bind antigens. Microporous structures generally are preferred, but materials with the gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes that cause covalent linkage of the antigen or antibody to the support. The irreversible binding of the antigen or antibody is obtained, however, in general, by adsorption on the porous material by hydrophobic forces.

After the lysis mixture suspected of containing or containing the immunosuppressant is brought into contact with the at least one first capture antibody, the resulting assay mixture is incubated to allow for the formation of a first capture antibody (or multiple antibody)-drug complex. The incubation can be carried out at any suitable pH, including a pH of from about 4.5 to about 10.0, at any suitable temperature, including from about 2° C. to about 45° C., and for a suitable time period from at least about one (1) minute to about eighteen (18) hours, preferably from about 4-20 minutes, most preferably from about 17-19 minutes.

After the addition of a detection agent and the formation of a labeled complex, the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of drug in the test sample can be determined by use of a standard curve that has been generated, for example, using serial dilutions of immunosuppressant drug of known concentration. Other than using serial dilutions of the drug, the standard curve can be generated gravimetric ally, by mass spectroscopy and by other techniques known in the art.

In a preferred forward competitive format, an aliquot of labeled drug, or analogue thereof, of a known concentration is used to compete with the drug present in a test sample for binding to the antibody. In a forward competition assay, an immobilized antibody can either be sequentially or simultaneously contacted with the test sample and a labeled drug or drug analogue thereof. The drug or drug analogue can be labeled with any suitable detectable label, including those detectable labels discussed above. In this assay, the capture antibody can be immobilized on to a solid support using the techniques discussed previously herein. Alternatively, the capture antibody can be coupled to an antibody, such as an antispecies antibody, that has been immobilized on to a solid support, such as a microparticle.

The labeled drug or drug analogue, the lysis mixture and the antibody are incubated under conditions similar to those described above in connection with the sandwich assay format. Two different types of antibody-drug complexes are then generated. Specifically, one of the antibody-drug complexes generated contains a detectable label while the other antibody-drug complex does not contain a detectable label. The antibody-drug complex can be, but does not have to be, separated from the remainder of the assay mixture prior to quantification of the detectable label. Regardless of whether the antibody-drug complex is separated from the remainder of the assay mixture, the amount of detectable label in the antibody-drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

The antibody-drug complex can be separated from the assay mixture by binding the antibody to a solid support, such as the solid supports discussed above in connection with the sandwich assay format, and then removing the remainder of the assay mixture from contact with the solid support.

In a reverse competition assay, an immobilized immunosuppressant drug or analogue thereof can either be sequentially or simultaneously contacted with a lysis mixture and at least one labeled antibody. The antibody can be labeled with any suitable detectable label, including those detectable labels discussed above. The drug or drug analogue can be bound to a solid support, such as the solid supports discussed above in connection with the sandwich assay format.

The immobilized drug or drug analogue, lysis mixture, and at least one labeled antibody are incubated under conditions similar to those described above in connection with the sandwich assay format. Two different types of antibody-drug complexes are then generated. Specifically, one of the antibody-drug complexes generated is immobilized and contains a detectable label while the other antibody-drug complex is not immobilized and contains a detectable label. The non-immobilized antibody-drug complex and the remainder of the assay mixture are removed from the presence of the immobilized antibody-drug complex through techniques known in the art, such as washing. Once the non-immobilized antibody-drug complex is removed, the amount of detectable label in the immobilized antibody-drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

In a capture-in-solution assay, soluble antibody can either be sequentially or simultaneously contacted with a lysis reagent mixture and at least one immobilized specific antibody. The specific antibody can be bound to a solid support, such as the solid supports discussed above in connection with the sandwich assay format.

The immobilized specific antibody, lysis reagent mixture, and at least one soluble antibody are incubated under conditions similar to those described above in connection with the sandwich assay format. Two different types of antibody-drug complexes are then generated. Specifically, one of the antibody-drug complexes generated is immobilized while the other antibody-drug complex is not immobilized. The non-immobilized antibody-drug complex and the remainder of the assay mixture are removed from the presence of the immobilized antibody-drug complex through techniques known in the art, such as washing. Once the non-immobilized antibody-drug complex is removed, labeled drug is added to the immobilized antibody-drug complex and is incubated under conditions similar to those described above. Unbound labeled drug is then removed from the presence of the immobilized antibody-drug-labeled drug complex through techniques known in the art, such as washing. Once the unbound labeled drug is removed, the amount of detectable label in the immobilized antibody-drug-labeled drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

The use of scanning probe microscopy (SPM) for immunoassays also is a technology to which the immunoassay methods of the present invention are easily adaptable. In SPM, in particular in atomic force microscopy, a capture agent is affixed to a solid phase having a surface suitable for scanning The capture agent can, for example, be adsorbed to a plastic or metal surface. Alternatively, the capture agent can be covalently attached to, e.g., derivatized plastic, metal, silicon, or glass according to methods known to those of ordinary skill in the art. Following attachment of the capture agent, the lysis mixture is contacted with the solid phase, and a scanning probe microscope is used to detect and quantify solid phase-affixed complexes. The use of SPM eliminates the need for labels which are typically employed in immunoassay systems. Such a system is described in U.S. application Ser. No. 662,147, which is incorporated herein by reference. This format can be used for a capture-in-solution immunoassay by substituting a binding partner for a capture agent for the capture agent. In this case, the capture agent becomes bound to the solid phase, via the binding partner, during the assay.

Immunoassays according to the invention can also be carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the invention is the Protiveris' multicantilever array. This array is based on chemo-mechanical actuation of specially designed silicon microcantilevers and subsequent optical detection of the microcantilever deflections. When coated on one side with a binding partner, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

In other embodiments, immunoassays according to the invention are carried out using electrochemical detection. A basic procedure for electrochemical detection has been described by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using PAPP volumes ranging from 20 µL to 360 µL have been reported previously. In capillary immunoassays with electrochemical detection, the lowest detection limit reported thus far is 3000 molecules of mouse IgG using a volume of 70 µL and a 30 minute or a 25 minute assay time.

Various electrochemical detection systems are described in U.S. Pat. No. 7,045,364 (issued May 16, 2006; incorporated herein by reference), U.S. Pat. No. 7,045,310 (issued May 16, 2006; incorporated herein by reference), U.S. Pat. No. 6,887,714 (issued May 3, 2005; incorporated herein by reference), U.S. Pat. No. 6,682,648 (issued Jan. 27, 2004; incorporated herein by reference); U.S. Pat. No. 6,670,115 (issued Dec. 30, 2003; incorporated herein by reference).

In particular embodiments, useful, for example, for simultaneously assaying multiple analytes in one test sample, the solid phase can include a plurality different capture agents or binding partners therefore.

Multiplex formats can, but need not, employ a plurality of labels, wherein each label is used for the detection of a particular analyte. For example, multiple, different analytes can be detected without using a plurality of labels where a plurality of capture agents or binding partners, such as antibodies, are affixed to the solid phase at different known locations, based on specificity. Because the specificity of the capture agent/binding partner at each location is known, the detection of a signal at a particular location can be associated with the presence of analyte bound at that location. Examples of this format include microfluidic devices and capillary arrays, containing different capture agents/binding partners at different locations along a channel or capillary, respectively, and microarrays, which typically contain different capture agents/binding partner arranged in a matrix of spots ("target elements") on a surface of a solid support. In particular embodiments, each different capture agent/binding partner can be affixed to a different electrode, which can, for example, be formed on a surface of a solid support, in a channel of a microfluidic device, or in a capillary.

III. Test Kits

The invention also provides test kits for assaying test samples for an analyte. Test kits according to the invention include one or more reagents useful for practicing one or more immunoassays according to the invention. A test kit generally includes a package with one or more containers holding the reagents, as one or more separate compositions or, optionally, as admixture where the compatibility of the reagents will allow. The test kit can also include other material(s), which may be desirable from a user standpoint, such as a buffer(s), a diluent(s), a standard(s), and/or any other material useful in sample processing, washing, or conducting any other step of the assay.

In particular embodiments, test kits of the invention can include: (a) a capture antibody; (b) a lysis reagent comprising a glycol selected from the group consisting of ethylene glycol, propylene glycol, and an analog thereof; and (c) immunoglobulins of an animal species that is the same as the animal species of the capture antibody. In certain embodiments, the immunoglobulins provided in the test kit are mouse immunoglobulins, such as, for example, non-specific polyclonal mouse IgG. The lysis reagent and immunoglobulins can, optionally, be combined and packaged in a single container. The test kit can additionally contain a solid phase including a solid-phase affixed binding partner for the capture antibody. The solid phase and the capture antibody can be packaged in the same or in separate containers. If desired, the test kit can also contain a control composition that includes the analyte being assayed.

In exemplary embodiments, useful for carrying out immunoassays for immunosuppressant drugs, the capture antibody can be specific for rapamycin (sirolimus), tacrolimus, everolimus, temsorolimus, zotarolimus, cyclosporine, or analogs of any of these compounds.

In certain embodiments, the lysis reagent includes the glycol at a concentration in the range of about 60% to about 80%. In particular embodiments, the immunoglobulins are present in the lysis reagent at a concentration in the range of about 90 μg/mL to 110 μg/mL. The lysis reagent can, optionally, include at least one alcohol having five or fewer carbons, such as methanol, ethanol, propanol, or a mixture of any of these alcohols. In variations of such embodiments, the ratio of glycol to alcohol can be in the range of about 4:1 to about 1:4, more particularly, in the range of about 4:1 to about 1:2.

In particular embodiments, test kits according to the invention can include one or more detergents and/or agents that release the analyte from one or more binding proteins in the test sample. Suitable detergents include non-ionic detergents, such as CHAPS, deoxycholate, and non-ionic detergents, such as saponin, as described above. Suitable releasing agents include agents that compete with the analyte for binding to one or more binding proteins, as described above, and proteases, which can be used to degrade binding proteins and liberate non-protein analytes. Exemplary proteases include proteinase K, subtilisin, dispase, thermolysin, trypsin, ficin, bromelain, and combinations thereof. Any detergents or proteases provided in kits of the invention should be provided in a manner that facilitates the production of a lysis mixture containing the components in suitable concentration, as described above.

Where such kits are to be employed for conducting sandwich immunoassays or competitive immunoassays, the kits can additionally include a labeled detection agent (e.g., labeled anti-analyte antibody or labeled analyte analog). In certain embodiments, the test kit includes at least one direct label, such as acridinium-9-carboxamide. Test kits according to the invention can also include at least one indirect label. If the label employed generally requires an indicator reagent to produce a detectable signal, the test kit preferably includes one or more suitable indicator reagents.

Test kits according to the invention preferably include instructions for carrying out one or more of the immunoassays of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

Of course, it goes without saying that any of the exemplary formats herein, and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott Laboratories' ARCHITECT®, AxSYM®, IMX®, ABBOTT PRISM®, and Quantum II platforms, as well as other platforms.

Additionally, the assays and kits of the present invention optionally can be adapted or optimized for point of care assay systems, including Abbott Laboratories' Point of Care (i-STAT®) electrochemical immunoassay system. Immunosensors and methods of manufacturing and operating them in single-use test devices are described, for example in U.S. Pat. No. 5,063,081 and published U.S. Patent Applications 20030170881, 20040018577, 20050054078, and 20060160164 (incorporated by reference herein for their teachings regarding same).

EXAMPLES

The following examples are offered to illustrate, but not to limit, the claimed invention.

Example 1

Homogeneous Capture-In-Solution: Calibration Curve Effect of Mouse IgG in Lysis Reagent This example illustrates the effect of the addition of mouse IgG in the lysis reagent in an automated immunoassay for cyclosporine.

The ARCHITECT® Cyclosporine assay (homogeneous concept-phase assay, Abbott Laboratories, Abbott Park, Ill.) was employed for these studies. The Anti-CsA monoclonal antibody used in the ARCHITECT assay is immobilized on Goat Anti-Mouse (GAM) coated magnetic microparticles, but is otherwise the same antibody used in soluble form in the Abbott TDx and AxSYM® assays (Abbott Laboratories, Abbott Park, Ill.). Soluble mouse anti-CsA antibody is added directly to GAM microparticles and non-covalent binding occurs by antibody-mediated binding. GAM particles can be prepared by anyone skilled in the art. Calibrated cyclosporine standards were prepared in a lysed whole blood diluent (IMx® Tacrolimus II Blood Diluent, Abbott Laboratories, Abbott Park, Ill.).

In the ARCHITECT® Cyclosporine assay, the amount of light (or signal) produced by a sample (typically following assay) is measured as relative light units (RLUs). RLU is the designation for the unit of optical measurement employed on the ARCHITECT® system, as well as in other instruments. The term RLU comes from the relation of the photon counting to a certain amount of signal-producing standard, such as acridinium. Each optics module is calibrated with a set of standards (e.g., acridinium standards). When the chemiluminescent reaction occurs, light is emitted and the photons are measured over a period of time (e.g., a 3 second time period). The photomultiplier tube (PMT) converts the photons counted to digital signal, which is then sent to a circuit board for processing. The optics circuit board converts the digital signal from the PMT to an analog signal that is proportional to the photons counted, which is in turn proportional to the amount of signal producing molecule (e.g., acridinium) present. This analog signal is then further processed to produce an RLU value. This relationship was established to produce a standard for calibration of the optics module, where the different standards have RLU values assigned to them. Thus, while the RLU unit itself is arbitrary, it is proportional (i.e., relative) to a certain amount of standard (e.g., acridinium).

Initial studies evaluated the effect on the cyclosporine calibration curve shape when mouse IgG was added to the lysis reagent. Results of these studies are shown in FIG. 5.

Figure 5:
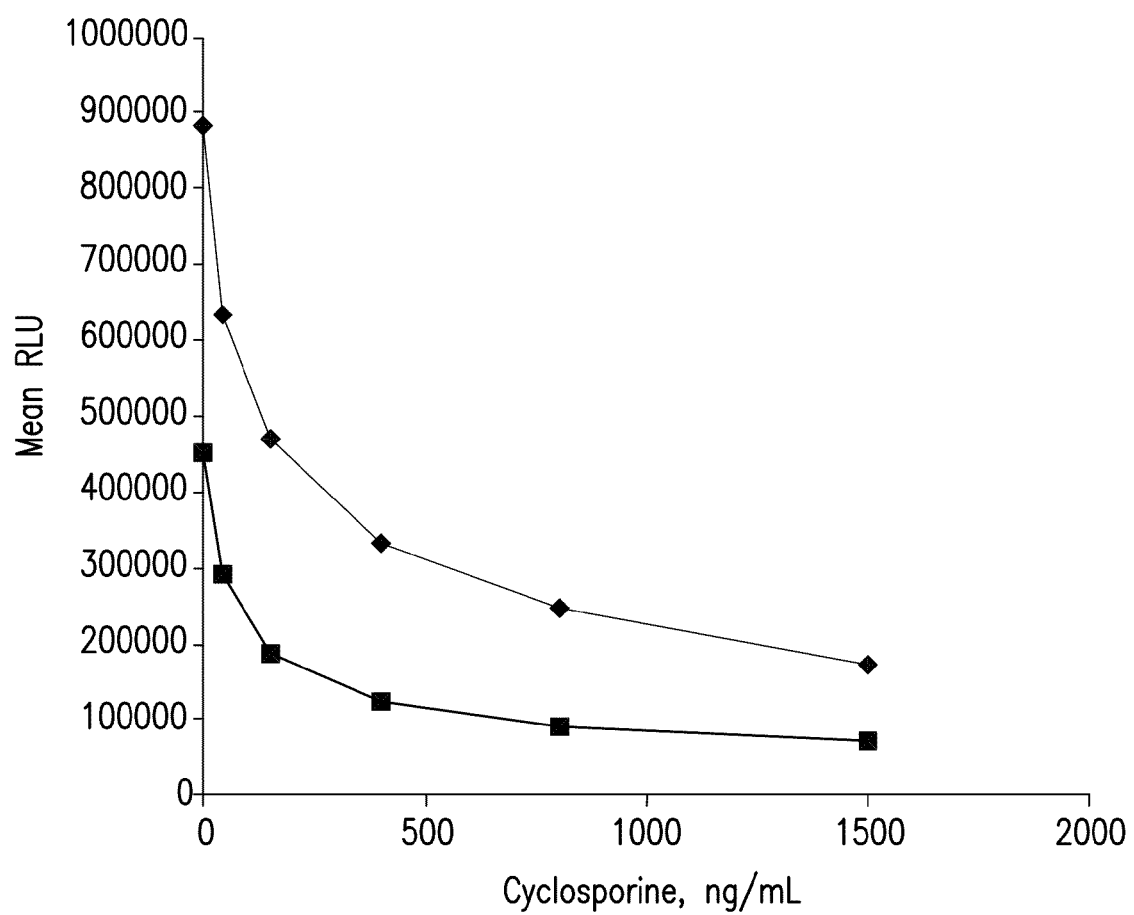
FIG. 5 is a graph obtained using an ARCHITECT® Cyclosporine Assay (Abbott Laboratories, Abbott Park, Ill.) tested with the lysis reagent comprising 70% ethylene glycol with or without 100 μg/mL mouse IgG. Abscissa: cyclosporine amount (ng/mL). Ordinate: signal (Relative light units, or RLUs). Symbols: (solid diamond), ethylene glycol only in the lysis reagent; (solid square), ethylene glycol and mouse IgG in the lysis reagent.

As can be seen from FIG. 5, with 70% ethylene glycol alone in the lysis reagent, a less favorable binding curve (less sensitive) was obtained than when 100 μg/mL mouse IgG was included with the ethylene glycol. These results confirm that the mouse IgG, when included in the lysis reagent along with ethylene glycol, is able to provide improved Cyclosporine calibration curves.

Example 2

Homogeneous Capture-In-Solution: Effect of Mouse IgG in Lysis Reagent on Reduction of HAMA Interference This example illustrates the effect of the addition of mouse IgG in the lysis reagent for the prevention of human anti-mouse antibody ("HAMA") interference in a Capture-in-Solution assay that utilizes a single step homogenous sample pretreatment.

For these studies, the impact of mouse IgG addition to the lysis reagent in an ARCHITECT® Cyclosporine assay was explored in terms of potentially blocking HAMA interference that may be present in transplant patient specimens. The ARCHITECT® homogeneous Capture-in-Solution cyclosporine assay format utilizes three assay reagents: (1) an assay specific diluent containing anti-cyclosporine monoclonal antibody, (2) a microparticle reagent consisting of goat anti-mouse immunoglobulin ("GAM")-coated magnetic microparticles, and (3) an acridinium-conjugated cyclosporine tracer for detection. Mouse IgG may be added to assay reagents in μg/mL to mg/mL concentrations in order to prevent potential assay interference from the presence of HAMA in some patient specimens. However, addition of excess mouse IgG to either the assay specific diluent or the microparticle reagent in the Capture-in-Solution assay would result in significant signal reduction, due to the fact that the ratio of mouse IgG to specific anti-cyclosporine monoclonal antibody could be more than a thousand-fold. Therefore, the possibility of adding non-specific polyclonal mouse IgG to the lysis reagent such that any HAMA present in the patient specimen could be bound up by the excess mouse IgG and not affect specific signal production was explored. The quantity of mouse IgG added to the lysis reagent and the amount of GAM antibody coating the microparticles would have to be balanced such that (1) there was sufficient mouse IgG present to bind HAMA, and (2) the mouse IgG did not out-compete with the mouse anti-cyclosporine monoclonal antibody for binding sites on the GAM-coated microparticles. A reduced amount of IgG effective at blocking HAMA was sought in conjunction with an increase in the amount of GAM coating the microparticles in an effort to overcome the impact of the mouse IgG on blocking the binding of specific mouse anti-cyclosporine antibody to the GAM microparticle capture antibody.

Results of exemplary experiments are shown in Table 1. Each reaction was carried out in a sample volume of 75 μL (total reaction volume of 215 μL), with 200 ng/mL mouse anti-cyclosporine Mab added as capture agent to the assay specific diluent, with microparticles coated at either 125 μg/mL GAM or 200 μg/mL GAM, and 100 μg/mL of polyclonal mouse IgG in the lysis reagent. The ratio of polyclonal mouse IgG to mouse anti-cyclosporine MAb is 500 in this example.

HAMA (Bioreclamation Inc., Hicksville, N.Y.) was spiked into low (90 ng/mL CsA), medium (250 ng/mL), and high (900 ng/mL) cyclosporine whole blood controls at final concentrations of either 10 or 100 μg/mL. Phosphate Buffered Saline was spiked into the cyclosporine controls at similar volumes to the HAMA in order to correct for analyte dilution.

TABLE 1

| | | GAM-125 | | GAM-200 | |
|---|---|---|---|---|---|
| Sample ID | Spike | CsA (ng/mL) | Spike as % Control PBS | CsA (ng/mL) | Spike as % Control PBS |
| Low | None | 103.3 | | 113.8 | |
| Med | | 246.4 | | 270.1 | |
| High | | 1033.6 | | 951.9 | |
| Low PBS | PBS | 99.9 | | 102.2 | |
| Med PBS | | 284.3 | | 241.1 | |
| High PBS | | 1013.3 | | 907.6 | |
| Low 10 | 10 μg/mL | 94.9 | −5.1 | 102.8 | 0.6 |
| Med 10 | HAMA | 251.1 | −11.7 | 260.2 | 7.9 |
| High 10 | | 922.8 | −8.9 | 999.5 | 10.1 |
| Mean | | | −8.6 | | 6.2 |
| Low 100 | 100 μg/mL | 83.1 | −16.8 | 87.3 | −14.5 |
| Med 100 | HAMA | 211.7 | −25.5 | 237.6 | −1.4 |
| High 100 | | 824.2 | −18.7 | 1045.9 | 15.2 |
| Mean | | | −20.3 | | −0.3 |

As can be seen from Table 1, GAM in an amount of either 125 μg/mL or 200 μg/mL resulted in acceptable Cyclosporine assay results. These results confirm that the mouse IgG, when included in the lysis reagent along with ethylene glycol, is able to provide improved Cyclosporine Assay results, by blocking up to 10 μg/mL HAMA.

Example 3

Homogeneous Capture-in-Solution: Effect of Buffer in the Lysis Reagent

This example illustrates the effect of the addition of buffer to lysis reagent in an automated immunoassay for cyclosporine.

Generally speaking, the effect of a buffer on antibody performance (e.g., antibody binding) is dependent on the pI of an antibody. For a polyclonal antibody such as the polyclonal mouse IgG, calculation of a pI is not possible. However, buffer appears to be necessary at least for long-term stability of the polyclonal mouse IgG, inasmuch as such IgG dissolved in water alone ultimately precipitates out of solution.

Figure 6:
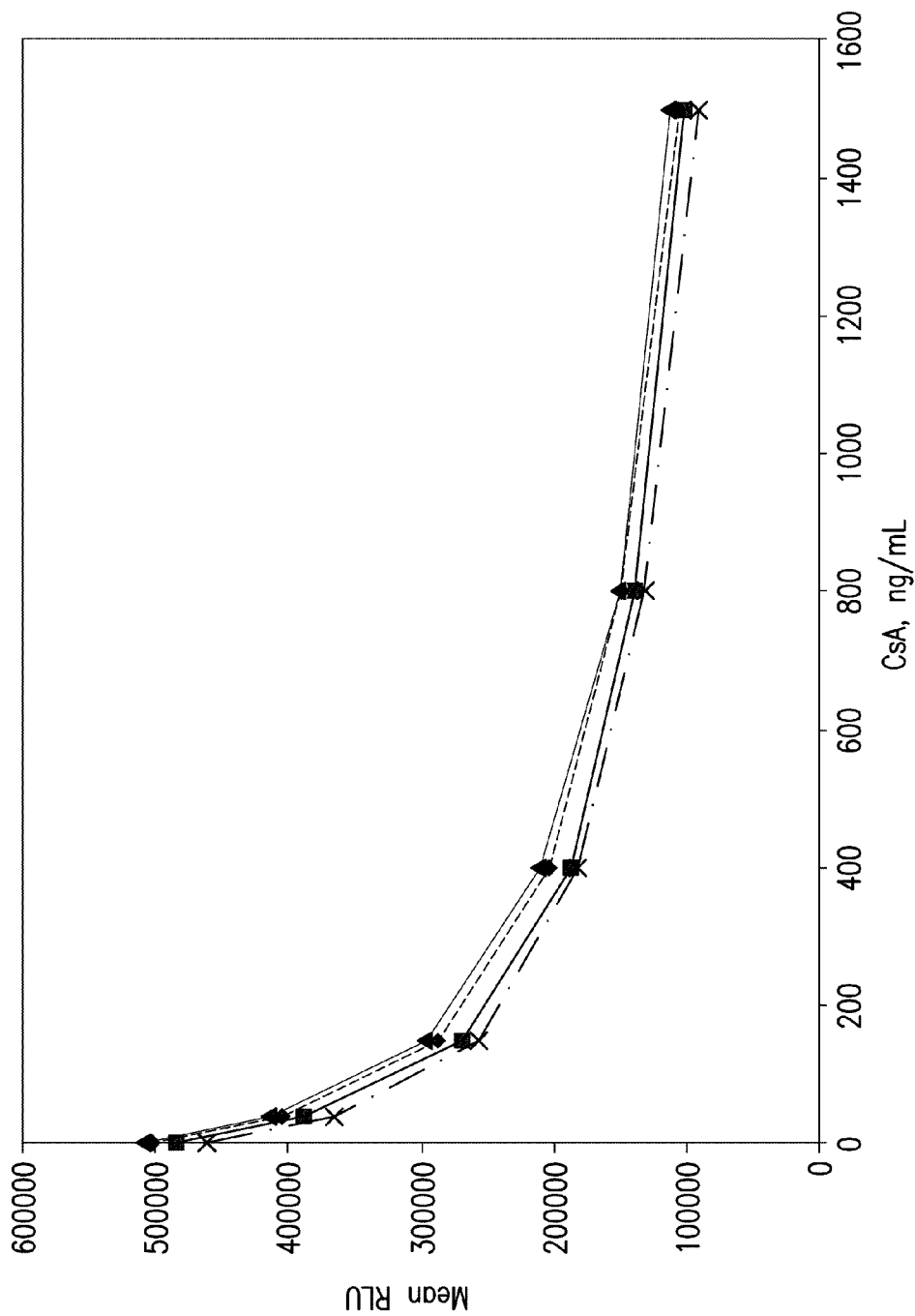
FIG. 6 is a graph obtained using an ARCHITECT® Cyclosporine Assay (Abbott Laboratories, Abbott Park, Ill.) tested with the lysis reagent comprising: 70% ethylene glycol, 100 μg/mL mouse IgG in either 30% distilled water or 30% Tris (pH 7.5 or 8.0) or TEA buffer (pH 8.0). Abscissa: cyclosporine amount (ng/mL). Ordinate: signal (Relative light units, or RLUs). Symbols: (solid diamond), Tris buffer, pH 8.0; (solid square), Tris buffer, pH 7.5; (solid triangle), TEA buffer, pH 8.0; (-x-), water.

Results of exemplary experiments are shown in FIG. 6. Each reaction was carried out in a sample volume of 35 μL (total reaction volume of 165 μL), with 200 ng/mL anti-cyclosporine Mab added as capture agent to the assay diluent, and microparticles coated with either GAM in an amount of 125 µg/mL present in a bovine serum albumin diluent. The anti-cyclosporine monoclonal antibody used in the ARCHITECT® assay as described herein is immobilized on GAM-coated magnetic microparticles, but is otherwise the same antibody used in soluble form in the Abbott TDx and ABBOTT AxSYM® assays (Abbott Laboratories, Abbott Park, Ill.). The lysis reagent comprised: 70% ethylene glycol, 100 µg/mL mouse IgG in either 30% distilled water or 30% Tris (pH 7.5 or 8.0) or TEA buffer (pH 8.0).

As can be seen from FIG. 6, both Tris and TEA buffer, at a pH of from about 7.0 to about 8.0 in the lysis reagent containing the polyclonal mouse IgG resulted in the generation of acceptable cyclosporine calibration curves. In addition, inspection of the TEA buffered lysis reagent did not visually identify any precipitation of the mouse IgG after two weeks storage at room temperature.

It is understood that the examples and embodiments described herein are for illustrative purposes only and that various modifications or changes in light thereof will be suggested to persons skilled in the art and are to be included within the spirit and purview of this application and scope of the appended claims.

In addition, the commonly owned, co-pending application U.S. Provisional Application Ser. No. 60/882,732 filed on Dec. 29, 2006 is explicitly incorporated by reference in its entirety for its teachings regarding a diagnostic test for the detection of a molecule or drug in whole blood.

The commonly owned, co-pending application U.S. Non-provisional application Ser. No. 11/618,495 filed on Dec. 29, 2006 is explicitly incorporated by reference in its entirety for its teachings regarding a non-denaturing lysis reagent.

The commonly owned, co-pending application U.S. Provisional Application Ser. No. 60/882,863 filed on Dec. 29, 2006 is explicitly incorporated by reference in its entirety for its teachings regarding an improved assay for immunosuppressant drugs.

The commonly owned, co-pending application U.S. Non-provisional application Ser. No. 11/490,624 filed on Jul. 21, 2006 is explicitly incorporated by reference in its entirety for its teachings regarding an extractive reagent composition.

In addition, all other publications, patents, and patent applications cited herein are hereby incorporated by reference in their entirety for all purposes.

What is claimed is:

1. A lysis reagent mixture for use in an immunoassay employing a capture antibody, the lysis reagent mixture comprising:
    a glycol selected from the group consisting of ethylene glycol, propylene glycol, and an analog thereof; and
    immunoglobulins of an animal species that is the same as the animal species of the capture antibody.

2. The lysis reagent mixture of claim 1, wherein the mixture additionally comprises a test sample suspected of comprising antibodies specific for said immunoglobulins.

3. The lysis reagent mixture of claim 2, wherein the test sample comprises a human blood sample.

4. The lysis reagent mixture of claim 1, wherein the immunoglobulins are mouse immunoglobulins.

5. The lysis reagent mixture of claim 4, wherein the mouse immunoglobulins comprise non-specific polyclonal mouse IgG.

6. The lysis reagent mixture of claim 5, wherein the glycol is present in the lysis reagent mixture (after addition of test sample) at a concentration in the range of about 15 % to about 20 %.

7. The lysis reagent mixture of claim 2, wherein the immunoglobulins are present in the lysis reagent mixture (after addition of test sample) at a concentration in the range of about 20 µg/mL to 30 µg/mL.

8. The lysis reagent mixture of claim 5, wherein the lysis reagent mixture additionally comprises at least one alcohol having five or fewer carbons.

9. The lysis reagent mixture of claim 5, wherein the lysis reagent mixture additionally comprises a buffer at pH in the range of about 7.0 to about 8.0.

10. The lysis reagent mixture of claim 5, wherein the lysis reagent mixture additionally comprises a detergent.

11. A test kit for use in an immunoassay, the test kit comprising:
    (a) a capture antibody;
    (b) a lysis reagent comprising a glycol selected from the group consisting of ethylene glycol, propylene glycol, and an analog thereof; and
    (c) immunoglobulins of an animal species that is the same as the animal species of the capture antibody.

12. The test kit of claim 11, wherein the lysis reagent and immunoglobulins are combined and packaged in a single container.

13. The test kit of claim 11, additionally comprising a solid phase including a solid-phase affixed binding partner for the capture antibody, wherein the solid phase and the capture antibody are packaged in separate containers.

14. The test kit of claim 11, wherein the immunoglobulins are mouse immunoglobulins.

15. The test kit of claim 14, wherein the mouse immunoglobulins comprise non-specific polyclonal mouse IgG.

16. The test kit of claim 11, wherein the capture antibody is capable of binding to at least one immunosuppressant drug.

17. The test kit of claim 16, wherein the immunosuppressant drug is selected from the group consisting of sirolimus, tacrolimus, everolimus, temsorolimus, zotarolimus, cyclosporine, and analogs of any of these compounds.

18. The test kit of claim 11, additionally comprising a control composition comprising the at least one analyte of (a).

19. The test kit of claim 11, wherein the glycol is present in the lysis reagent at a concentration in the range of about 60% to about 80%.

20. The test kit of claim 12, wherein the immunoglobulins are present in the lysis reagent at a concentration in the range of about 90 µg/mL to 110 µg/mL.

21. The test kit of claim 11, wherein the lysis reagent additionally comprises at least one alcohol having five or fewer carbons.

22. The test kit of claim 11, wherein the lysis reagent additionally comprises a buffer at pH in the range of about 7.0 to about 8.0.

23. The test kit of claim 11, additionally comprising a detergent.

24. The test kit of claim 11, wherein the test kit additionally comprises an agent that releases the analyte from one or more binding proteins in the test sample.

25. The test kit claim 24, wherein the agent competes with the analyte for binding to said one or more binding proteins.

26. The test kit claim 25, wherein the analyte comprises an immunosuppressant drug and the agent comprises a different, but structurally similar, immunosuppressant drug.

27. The test kit claim 24, wherein the agent comprises a protease that degrades said one or more binding proteins.

28. A test kit comprising:
    (a) a capture antibody capable of binding specifically to at least one immunosuppressant drug selected from the group consisting of sirolimus, tacrolimus, everolimus, temsorolimus, zotarolimus and cyclosporine;

(b) a lysis reagent comprising:

a glycol selected from the group consisting of ethylene glycol, propylene glycol, and an analog thereof; and immunoglobulins of an animal species that is the same as the animal species of a capture antibody that binds the analyte;

(c) a solid phase including a solid-phase affixed binding partner for the capture antibody, wherein the solid phase and the capture antibody are provided in separate containers; and (d) a control composition comprising the at least one immunosuppressant drug of (a).

29. The test kit of claim 28, wherein the at least one immunosuppressant drug comprises cyclosporine.

* * * * *